(12) United States Patent
Janna et al.

(10) Patent No.: US 8,814,868 B2
(45) Date of Patent: Aug. 26, 2014

(54) INSTRUMENTED ORTHOPAEDIC IMPLANT FOR IDENTIFYING A LANDMARK

(75) Inventors: Sied W. Janna, Memphis, TN (US); Darren J. Wilson, York (GB); Robert L. Morgan, York (GB)

(73) Assignee: Smith & Nephew, Inc., Memphis, TN (US)

( * ) Notice: Subject to any disclaimer, the term of this patent is extended or adjusted under 35 U.S.C. 154(b) by 427 days.

(21) Appl. No.: 12/528,253

(22) PCT Filed: Feb. 28, 2007

(86) PCT No.: PCT/US2007/063001
§ 371 (c)(1),
(2), (4) Date: Feb. 12, 2010

(87) PCT Pub. No.: WO2008/105874
PCT Pub. Date: Sep. 4, 2008

(65) Prior Publication Data
US 2010/0145337 A1    Jun. 10, 2010

(51) Int. Cl.
*A61B 17/58* (2006.01)
*A61B 19/00* (2006.01)
*A61B 17/17* (2006.01)
*A61B 17/72* (2006.01)

(52) U.S. Cl.
CPC ....... *A61B 17/1707* (2013.01); *A61B 2019/547* (2013.01); *A61B 19/5244* (2013.01); *A61B 17/72* (2013.01); *A61B 17/1725* (2013.01)
USPC ............................................. 606/67; 128/899

(58) Field of Classification Search
USPC ................. 606/62, 67, 424; 128/899
See application file for complete search history.

(56) References Cited

U.S. PATENT DOCUMENTS

| 3,219,969 | A | 11/1965 | Snavely |
| 4,353,110 | A | 10/1982 | Ellis |
| 4,532,599 | A | 7/1985 | Smith |
| 4,621,628 | A | 11/1986 | Brudermann |

(Continued)

FOREIGN PATENT DOCUMENTS

| CN | 2698283 Y | 5/2005 |
| DE | 102008023760 | 12/2009 |

(Continued)

OTHER PUBLICATIONS

Office Action for Chinese Application No. 200880006490.9, mailed Mar. 31, 2011, 13 pages.

(Continued)

*Primary Examiner* — Ellen C Hammond
*Assistant Examiner* — Stuart S Bray
(74) *Attorney, Agent, or Firm* — Fish & Richardson P.C.

(57) ABSTRACT

A system (110, 150) for targeting a landmark (114, 160) is disclosed. The system includes an instrumented medical implant (112, 152), a control circuit (118, 153), a power supply (120, 157), and a landmark identifier (122, 154). The instrumented medical implant (112, 152) has one or more landmarks (114, 160) and each landmark (114, 160) has a corresponding coil (116, 162). The control circuit (118, 153) is electrically connected to the corresponding coil (116, 162), and the power supply (120, 157) is electrically connected to the control circuit (118,153). The landmark identifier (122, 154) has a magnetic sensor (124, 155) for sensing the corresponding coil (116, 162).

27 Claims, 12 Drawing Sheets

(56) References Cited

U.S. PATENT DOCUMENTS

| | | | |
|---|---|---|---|
| D297,047 S | 8/1988 | Hon et al. | |
| 4,794,930 A | 1/1989 | Machida et al. | |
| 4,803,976 A | 2/1989 | Frigg et al. | |
| 5,049,151 A | 9/1991 | Durham et al. | |
| 5,127,913 A | 7/1992 | Thomas, Jr. | |
| 5,217,009 A | 6/1993 | Kronberg | |
| 5,251,127 A | 10/1993 | Raab | |
| 5,281,224 A | 1/1994 | Faccioli et al. | |
| 5,361,766 A | 11/1994 | Nichols et al. | |
| 5,383,917 A | 1/1995 | Desai et al. | |
| 5,411,503 A | 5/1995 | Hollstien et al. | |
| 5,417,688 A | 5/1995 | Elstrom et al. | |
| 5,433,720 A | 7/1995 | Faccioli et al. | |
| 5,514,145 A | 5/1996 | Durham et al. | |
| 5,580,156 A | 12/1996 | Suzuki et al. | |
| 5,584,838 A | 12/1996 | Rona et al. | |
| 5,585,783 A | 12/1996 | Hall | |
| 5,957,836 A | 9/1999 | Johnson | |
| 5,957,934 A | 9/1999 | Rapoport | |
| 6,009,878 A | 1/2000 | Weijand et al. | |
| 6,036,696 A | 3/2000 | Lambrecht et al. | |
| 6,039,742 A | 3/2000 | Krettek et al. | |
| 6,074,394 A | 6/2000 | Krause | |
| 6,081,741 A | 6/2000 | Hollis | |
| 6,106,528 A | 8/2000 | Durham et al. | |
| 6,157,853 A | 12/2000 | Blume et al. | |
| 6,162,228 A | 12/2000 | Durham | |
| 6,174,335 B1 | 1/2001 | Varieur et al. | |
| 6,212,419 B1 | 4/2001 | Blume et al. | |
| 6,233,490 B1 | 5/2001 | Kasevich | |
| 6,267,770 B1 | 7/2001 | Truwit | |
| 6,304,091 B1 | 10/2001 | Shahoian et al. | |
| 6,311,082 B1 | 10/2001 | Creighton, IV et al. | |
| 6,474,341 B1 | 11/2002 | Hunter et al. | |
| 6,503,249 B1 | 1/2003 | Krause | |
| 6,575,973 B1 | 6/2003 | Shekalim | |
| 6,636,757 B1 | 10/2003 | Jascob et al. | |
| 6,675,491 B2 | 1/2004 | Ooyama et al. | |
| 6,694,168 B2 | 2/2004 | Traxel et al. | |
| 6,718,194 B2 | 4/2004 | Kienzle, III | |
| 6,747,253 B1 | 6/2004 | Firth et al. | |
| 6,807,446 B2 | 10/2004 | Fenn et al. | |
| 6,890,332 B2 | 5/2005 | Truckai et al. | |
| 6,991,655 B2 | 1/2006 | Iversen | |
| 7,001,346 B2 | 2/2006 | White | |
| 7,029,478 B2 | 4/2006 | Hollstien et al. | |
| 7,060,075 B2 * | 6/2006 | Govari et al. | 606/98 |
| D528,211 S | 9/2006 | Solar et al. | |
| 7,130,676 B2 | 10/2006 | Barrick | |
| 7,152,608 B2 | 12/2006 | Hunter et al. | |
| 7,217,276 B2 | 5/2007 | Henderson et al. | |
| 7,253,611 B2 | 8/2007 | Ma et al. | |
| 7,294,133 B2 | 11/2007 | Zink et al. | |
| 7,295,184 B2 | 11/2007 | Suprun et al. | |
| 7,358,481 B2 | 4/2008 | Yeoh et al. | |
| 7,477,926 B2 | 1/2009 | McCombs | |
| 7,532,997 B2 | 5/2009 | Li et al. | |
| 7,542,791 B2 | 6/2009 | Mire et al. | |
| 7,549,960 B2 * | 6/2009 | Govari | 600/437 |
| 7,559,931 B2 | 7/2009 | Stone | |
| 7,575,550 B1 | 8/2009 | Govari | |
| 7,634,306 B2 | 12/2009 | Sarin et al. | |
| 7,686,818 B2 * | 3/2010 | Simon et al. | 606/130 |
| 7,702,379 B2 | 4/2010 | Avinash et al. | |
| 7,727,240 B1 | 6/2010 | Benton | |
| 7,729,742 B2 * | 6/2010 | Govari | 600/424 |
| 7,780,681 B2 | 8/2010 | Sarin et al. | |
| 7,785,330 B2 | 8/2010 | Sherman et al. | |
| 7,835,785 B2 * | 11/2010 | Scully et al. | 600/424 |
| 7,840,254 B2 | 11/2010 | Glossop | |
| 7,846,162 B2 | 12/2010 | Nelson et al. | |
| 7,918,853 B2 | 4/2011 | Watanabe et al. | |
| 7,925,068 B2 * | 4/2011 | Hoctor et al. | 382/132 |
| 7,927,338 B2 | 4/2011 | Laffargue et al. | |
| 7,949,386 B2 | 5/2011 | Buly et al. | |
| 7,955,280 B2 | 6/2011 | Radinsky et al. | |
| 8,007,448 B2 | 8/2011 | Moctezuma | |
| 8,066,706 B2 * | 11/2011 | Schlienger et al. | 606/64 |
| 8,167,823 B2 | 5/2012 | Nycz et al. | |
| 8,197,494 B2 * | 6/2012 | Jaggi et al. | 606/130 |
| 8,211,108 B2 | 7/2012 | Matityahu | |
| 8,241,296 B2 | 8/2012 | Wasielewski | |
| 8,301,262 B2 | 10/2012 | Mi et al. | |
| 8,337,426 B2 | 12/2012 | Nycz | |
| 8,623,023 B2 | 1/2014 | Ritchey et al. | |
| 2002/0032445 A1 * | 3/2002 | Fujiwara | 606/67 |
| 2002/0052604 A1 * | 5/2002 | Simon et al. | 606/62 |
| 2002/0077540 A1 | 6/2002 | Kienzle, III | |
| 2002/0173792 A1 * | 11/2002 | Severns et al. | 606/62 |
| 2003/0105470 A1 | 6/2003 | White | |
| 2003/0120150 A1 | 6/2003 | Govari | |
| 2003/0135211 A1 * | 7/2003 | Cho | 606/62 |
| 2003/0153829 A1 | 8/2003 | Sarin et al. | |
| 2003/0164172 A1 | 9/2003 | Chumas et al. | |
| 2003/0208122 A1 | 11/2003 | Melkent et al. | |
| 2004/0011365 A1 * | 1/2004 | Govari et al. | 128/899 |
| 2004/0034355 A1 * | 2/2004 | Govari et al. | 606/72 |
| 2004/0097952 A1 | 5/2004 | Sarin et al. | |
| 2004/0147926 A1 | 7/2004 | Iversen | |
| 2004/0230199 A1 | 11/2004 | Jansen et al. | |
| 2004/0243148 A1 | 12/2004 | Wasielewski | |
| 2004/0254584 A1 | 12/2004 | Sarin et al. | |
| 2005/0027301 A1 | 2/2005 | Stihl | |
| 2005/0027304 A1 | 2/2005 | Leloup et al. | |
| 2005/0035115 A1 | 2/2005 | Anderson et al. | |
| 2005/0035116 A1 | 2/2005 | Brown et al. | |
| 2005/0043726 A1 | 2/2005 | McHale et al. | |
| 2005/0059885 A1 | 3/2005 | Melkent et al. | |
| 2005/0070916 A1 | 3/2005 | Hollstien et al. | |
| 2005/0075562 A1 | 4/2005 | Szakelyhidi et al. | |
| 2005/0075632 A1 | 4/2005 | Russell et al. | |
| 2005/0080335 A1 * | 4/2005 | Simon et al. | 600/424 |
| 2005/0080427 A1 * | 4/2005 | Govari et al. | 606/98 |
| 2005/0085714 A1 | 4/2005 | Foley et al. | |
| 2005/0085715 A1 | 4/2005 | Dukesherer et al. | |
| 2005/0099290 A1 | 5/2005 | Govari | |
| 2005/0124988 A1 | 6/2005 | Terrill-Grisoni et al. | |
| 2005/0143726 A1 | 6/2005 | Bortkiewicz | |
| 2005/0148855 A1 | 7/2005 | Kienzle | |
| 2005/0149050 A1 | 7/2005 | Stifter et al. | |
| 2005/0197569 A1 | 9/2005 | McCombs | |
| 2005/0228270 A1 | 10/2005 | Lloyd et al. | |
| 2005/0242087 A1 | 11/2005 | Anderson et al. | |
| 2005/0245821 A1 | 11/2005 | Govari et al. | |
| 2005/0261700 A1 | 11/2005 | Tuma et al. | |
| 2006/0015031 A1 | 1/2006 | Kienzle | |
| 2006/0029186 A1 | 2/2006 | De Villiers et al. | |
| 2006/0052782 A1 | 3/2006 | Morgan et al. | |
| 2006/0074405 A1 | 4/2006 | Malackowski et al. | |
| 2006/0084867 A1 | 4/2006 | Tremblay et al. | |
| 2006/0095047 A1 | 5/2006 | de la Barrera | |
| 2006/0106400 A1 | 5/2006 | Fernandez et al. | |
| 2006/0142656 A1 * | 6/2006 | Malackowski et al. | 600/424 |
| 2006/0190011 A1 | 8/2006 | Ries | |
| 2006/0264731 A1 | 11/2006 | Murphy | |
| 2006/0282168 A1 | 12/2006 | Sherman et al. | |
| 2006/0287613 A1 | 12/2006 | Amiot et al. | |
| 2006/0293593 A1 | 12/2006 | Govari et al. | |
| 2006/0293614 A1 | 12/2006 | Radinsky et al. | |
| 2007/0093709 A1 | 4/2007 | Abernathie | |
| 2007/0129629 A1 | 6/2007 | Beauregard et al. | |
| 2007/0162018 A1 | 7/2007 | Jensen et al. | |
| 2007/0167744 A1 | 7/2007 | Beauregard et al. | |
| 2007/0191827 A1 | 8/2007 | Lischinsky et al. | |
| 2007/0208251 A1 | 9/2007 | Anderson et al. | |
| 2007/0225595 A1 | 9/2007 | Malackowski et al. | |
| 2007/0249967 A1 | 10/2007 | Buly et al. | |
| 2007/0255132 A1 | 11/2007 | Shalgi et al. | |
| 2007/0276370 A1 | 11/2007 | Altarac et al. | |
| 2007/0282440 A1 | 12/2007 | Visentin | |
| 2008/0015551 A1 | 1/2008 | Feine | |
| 2008/0021309 A1 | 1/2008 | Amiot et al. | |
| 2008/0039857 A1 | 2/2008 | Giersch et al. | |
| 2008/0051910 A1 | 2/2008 | Kammerzell et al. | |

(56) References Cited

U.S. PATENT DOCUMENTS

| | | |
|---|---|---|
| 2008/0071142 A1 | 3/2008 | Gattani et al. |
| 2008/0086145 A1 | 4/2008 | Sherman et al. |
| 2008/0146969 A1 | 6/2008 | Kurtz |
| 2008/0154266 A1 | 6/2008 | Protopsaltis et al. |
| 2008/0221628 A1* | 9/2008 | Milbocker et al. .......... 606/86 R |
| 2008/0228195 A1 | 9/2008 | von Jako et al. |
| 2008/0255560 A1 | 10/2008 | Myers et al. |
| 2008/0269596 A1 | 10/2008 | Revie et al. |
| 2008/0281326 A1* | 11/2008 | Watanabe et al. ............... 606/62 |
| 2008/0281334 A1 | 11/2008 | Zheng et al. |
| 2009/0024023 A1 | 1/2009 | Welches et al. |
| 2009/0054910 A1 | 2/2009 | Zheng et al. |
| 2009/0088756 A1 | 4/2009 | Anderson |
| 2009/0099404 A1 | 4/2009 | Kraus et al. |
| 2009/0138019 A1 | 5/2009 | Wasielewski |
| 2009/0165573 A1 | 7/2009 | Ledoux et al. |
| 2009/0177080 A1* | 7/2009 | Kristan et al. ............... 600/424 |
| 2009/0227862 A1 | 9/2009 | Smith et al. |
| 2009/0306665 A1 | 12/2009 | Lerner et al. |
| 2009/0306666 A1 | 12/2009 | Czartoski et al. |
| 2009/0326537 A1 | 12/2009 | Anderson |
| 2010/0041985 A1 | 2/2010 | Simon et al. |
| 2010/0063508 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0100011 A1 | 4/2010 | Roche |
| 2010/0137869 A1 | 6/2010 | Borja et al. |
| 2010/0137871 A1 | 6/2010 | Borja |
| 2010/0145337 A1* | 6/2010 | Janna et al. ...................... 606/67 |
| 2010/0152566 A1 | 6/2010 | Rains et al. |
| 2010/0152573 A1 | 6/2010 | Ritchey et al. |
| 2010/0211177 A1 | 8/2010 | Abdou |
| 2010/0249657 A1 | 9/2010 | Nycz et al. |
| 2010/0261998 A1 | 10/2010 | Stiehl |
| 2010/0274121 A1 | 10/2010 | Ritchey et al. |
| 2010/0274253 A1 | 10/2010 | Ure |
| 2010/0274256 A1 | 10/2010 | Ritchey et al. |
| 2010/0274306 A1 | 10/2010 | Pastore et al. |
| 2010/0289491 A1 | 11/2010 | Budker et al. |
| 2010/0312245 A1 | 12/2010 | Tipirneni et al. |
| 2011/0082366 A1* | 4/2011 | Scully et al. .................. 600/424 |
| 2011/0109311 A1 | 5/2011 | Walsh |
| 2011/0130765 A1 | 6/2011 | Fernandez et al. |
| 2011/0257518 A1 | 10/2011 | Buly et al. |
| 2011/0270080 A1* | 11/2011 | Crane ........................ 600/424 |
| 2011/0288600 A1 | 11/2011 | Ritchey et al. |
| 2011/0295108 A1* | 12/2011 | Cox et al. ...................... 600/424 |
| 2011/0295253 A1 | 12/2011 | Bonutti et al. |
| 2012/0010500 A1 | 1/2012 | Couture et al. |
| 2012/0022406 A1 | 1/2012 | Hladio et al. |
| 2012/0035468 A1* | 2/2012 | Ritchey et al. ............... 600/424 |
| 2012/0091122 A1 | 4/2012 | Ahmad et al. |
| 2012/0101361 A1 | 4/2012 | Rains et al. |
| 2012/0136402 A1 | 5/2012 | Burroughs |
| 2012/0143047 A1* | 6/2012 | Kimura et al. ............... 600/424 |
| 2012/0184844 A1* | 7/2012 | Gielen et al. .................. 600/424 |
| 2012/0209117 A1 | 8/2012 | Mozes et al. |
| 2012/0220107 A1 | 8/2012 | Fukuda et al. |
| 2012/0226094 A1 | 9/2012 | Ritchey et al. |
| 2012/0227542 A1 | 9/2012 | Koch |
| 2012/0232561 A1 | 9/2012 | Fernandez |
| 2012/0253354 A1 | 10/2012 | Arlettaz et al. |
| 2012/0283599 A1 | 11/2012 | Borja |
| 2013/0131679 A1 | 5/2013 | Janna et al. |
| 2013/0218007 A1 | 8/2013 | Petteys et al. |
| 2013/0289573 A1 | 10/2013 | Heilala |

FOREIGN PATENT DOCUMENTS

| | | |
|---|---|---|
| EP | 523905 | 5/1993 |
| EP | 628287 | 4/1995 |
| EP | 1391181 | 2/2004 |
| EP | 1570782 A2 | 9/2005 |
| EP | 1382308 | 11/2005 |
| EP | 1570781 | 9/2009 |
| EP | 2130511 | 12/2009 |
| EP | 1563810 B1 | 3/2010 |
| EP | 1743590 | 10/2010 |
| EP | 1803394 B1 | 1/2012 |
| GR | 1005791 | 1/2008 |
| WO | WO9500085 | 1/1995 |
| WO | WO9713467 | 4/1997 |
| WO | WO9832387 A1 | 7/1998 |
| WO | WO9947052 | 9/1999 |
| WO | WO0134016 | 10/2001 |
| WO | WO02062250 | 8/2002 |
| WO | WO03044556 A2 | 5/2003 |
| WO | WO03073951 A1 | 9/2003 |
| WO | WO03041611 A3 | 12/2003 |
| WO | WO03105659 | 12/2003 |
| WO | WO2004030556 A2 | 4/2004 |
| WO | WO2004001569 B1 | 7/2004 |
| WO | WO2004069063 | 8/2004 |
| WO | WO2004091419 A8 | 11/2004 |
| WO | WO2004112610 | 12/2004 |
| WO | WO2005023110 A1 | 3/2005 |
| WO | WO2005087125 A2 | 9/2005 |
| WO | WO2005120203 A2 | 12/2005 |
| WO | WO2006060632 A1 | 6/2006 |
| WO | WO2005084572 A3 | 11/2006 |
| WO | WO2007025191 | 3/2007 |
| WO | WO2007009088 A3 | 5/2007 |
| WO | WO2007061890 | 5/2007 |
| WO | WO2007061890 A2 | 5/2007 |
| WO | WO2006094119 A3 | 11/2007 |
| WO | WO2007133168 | 11/2007 |
| WO | WO2008105874 | 9/2008 |
| WO | WO2008106593 | 9/2008 |
| WO | WO2009046547 A1 | 4/2009 |
| WO | WO2009108214 | 9/2009 |
| WO | WO2009131999 | 10/2009 |
| WO | WO2010011978 A1 | 1/2010 |
| WO | WO2010028046 | 3/2010 |
| WO | WO2010099247 A2 | 9/2010 |
| WO | WO2010111272 A1 | 9/2010 |
| WO | WO2010129141 | 11/2010 |
| WO | WO2010129308 A2 | 11/2010 |
| WO | WO2011060536 A1 | 5/2011 |
| WO | WO2011124661 A1 | 10/2011 |
| WO | WO2012080840 A1 | 6/2012 |
| WO | WO2013049534 A1 | 4/2013 |

OTHER PUBLICATIONS

International Search Report and Written Opinion for International Application No. PCT/US2010/051678, mailed Apr. 14, 2011, 8 pages.
Ekliptik, Guiding Star, Lidis: The Best Solution for Distal Interlocking, 2008, 2 pages.
International Search Report for International Application No. PCT/US2008/055300, mailed Sep. 17, 2008, 3 pages.
International Preliminary Report on Patentability and Written Opinion for International Application No. PCT/US2008/055300, mailed Sep. 1, 2009, 6 pages.
International Preliminary Report on Patentability and Written Opinion for International Application No. PCT/US2007/063001, mailed Sep. 1, 2009, 5 pages.
International Search Report for International Application No. PCT/US2007/063001, mailed Nov. 30, 2007, 3 pages.
Rains, et al., U.S. Appl. No. 12/919,255, filed Aug. 25, 2010.
International Search Report for International Application No. PCT/US2008/074520, mailed Jan. 23, 2009, 2 pages.
Ekliptik, "Guiding Star", reprinted from http://ekliptik.si/content/view/37/42, on Jul. 1, 2010, 2 pages.
Ritchey, et al., U.S. Appl. No. 29/376,026, filed Sep. 30, 2010.
International Search Report and Written Opinion for International Application No. PCT/US2010/032634, mailed Jan. 26, 2011, 10 pages.
International Search Report and Written Opinion for PCT/US2010/030784, mailed Oct. 29, 2010, 11 pages.

(56) References Cited

OTHER PUBLICATIONS

European Search Report for European Application No. 07830964.7, mailed Jun. 18, 2010, 4 pages.
Office Action for European Application 08872996.7-1269, Jul. 21, 2011, 5 pages.
"Innomed Hip Instruments -hohmann retractors," reprinted from http://www.innomed.net/hip_rets_hohmanns.htm on Jan. 6, 2011, 8 pages.
Office Action for U.S. Appl. No. 12/547,716, mailed Apr. 2, 2012, 11 pages.
Office Action for U.S. Appl. No. 12/758,747, mailed Apr. 10, 2012, 11 pages.
Ex Parte Quayle Action in U.S. Appl. No. 29/376,026, mailed Apr. 30, 2012, 10 pages.
Office Action for U.S. Appl. No. 12/919,255, mailed May 25, 2012, 13 pages.
Office Action for U.S. Appl. No. 13/123,792, mailed Sep. 14, 2012.
Office Action for U.S. Appl. No. 13/323,010, mailed Aug. 14, 2012.
First Office Action for Chinese Application No. 200880128908.3 mailed Apr. 24, 2012.
Association of Surgical Technologists, "AST Recommended Standards of Practice for Surgical Drapes," effective Apr. 13, 2008.
Ashar, Tom, "Ultrasound Guidance for Placement of Central Venous Catheters," Israeli Journal of Emergency Medicine, vol. 7, No. 2, Jun. 2007.
Buckner, C., et al., "Real-Time Sonography wth Electromagnetic Tracking Navigation for Biopsy of a Hepatic Neoplasm Seen on on Arterial Phase Computed Tomography," J Ultrasound Med 2011, 30:253-256.
"GE Heathcare: Ultrasound Imaging Accessories, vol. 6," CIVco Medical Solutions, Multi-Modality Imaging, 2011.
"Guiding Star with the LIDIS module," Ekliptik, 2007.
Ekliptik, LIDIS module, brochure, 2010.
Brochure for GE Healthcare Drapes and Sterile Covers, accessed on Jun. 21, 2012, at http://www.gehealthcare.com/usen/xr/surgery/docs/SurgeryDrapes&Film.pdf.
Ekliptik, "User Manual: Guiding Star/LIDIS," Jun. 16, 2010, reprinted from http://www.ekliptik.si/html/downloads/documents/manuals/LIDIS_user_manual.pdf.
Medtronic, "Orthopaedic Navigation Soluations," 2005, reprinted from http://behzadisportsdoc.com/wordpress/wp-content/uploads/2011/05/medtronic_orthonaysolutions.pdf.
GE Healthcare, "Interventional X-ray, OEC C-arm," 2012.
International Search Report and Written Opinion for International Application PCT/US2012/022481, mailed Jul. 31, 2012.
Office Action for U.S. Appl. No. 12/547,716, mailed Sep. 18, 2012.
Office Action for U.S. Appl. No. 12/527,997, mailed Oct. 29, 2012.
Second Office Action for Chinese Application No. 200880006490.9 mailed Apr. 26, 2012.
Office Action for Australian Patent Application No. 2008221332, dated Jun. 15, 2012.
Office Action for U.S. Appl. No. 12/758,747, mailed Nov. 15, 2012.
Office Action for U.S. Appl. No. 12/919,255, mailed Jan. 8, 2013.
Office Action for U.S. Appl. No. 12/768,689, mailed Nov. 14, 2012.
Office Action for U.S. Appl. No. 12/768,689, mailed Jun. 5, 2012.
Notice of Reasons for Rejection for Japanese Application No. 2010-548660 mailed Jan. 15, 2013.
Notice of Reasons for Rejection for Japanese Application No. 2012-508518 mailed Dec. 10, 2013.
Office Action in Russian Application No. 2011146914, mailed Dec. 16, 2013.
Notice of Reasons for Rejection for Japanese Application No. 2012-508611, mailed Jan. 28, 2014.
Office Action for U.S. Appl. No. 13/030,801, mailed Mar. 13, 2013.
Office Action for U.S. Appl. No. 13/323,010, mailed Jun. 4, 2013.
Office Action for U.S. Appl. No. 12/527,997, mailed May 21, 2013.
International Search Report and Written Opinion for International Application No. PCT/US2012/041613, mailed Feb. 15, 2013.
International Search Report and Written Opinion for International Application No. PCT/US2013/027042, mailed Jun. 12, 2013.
Office Action for U.S. Appl. No. 13/123,792, mailed Jul. 2, 2013.
Communication Pursuant to Article 94(3) EPC for European Application No. 07757660.1, mailed Jun. 5, 2013.
Decision of Rejection for Japanese Application No. 2009-551851, mailed Jun. 11, 2013.
Communication Pursuant to Article 94(3) EPC for European Application No. 08730964.7, mailed Jun. 6, 2013.

\* cited by examiner

INSTRUMENTED ORTHOPAEDIC IMPLANT FOR IDENTIFYING A LANDMARK

CROSS-REFERENCE TO RELATED APPLICATIONS

This application is a U.S. National Phase filing of International Application No. PCT/US2007/063001. This prior application is herein incorporated by reference.

BACKGROUND OF THE INVENTION

1. Field of the Invention

The present invention relates generally to orthopaedic implants and more particularly to an instrumented orthopaedic implant for identifying a landmark.

2. Related Art

The interlocking femoral nail has significantly widened the scope for intramedullary (IM) fixation of long bone fractures. Locking an IM nail makes the construct more stable longitudinally and stops rotation of the nail within the bone. A typical IM nail fixation surgery involves a combination of jigs, x-ray imaging, and manual eye-balling to locate and drill the distal screw holes.

In this surgical procedure, an IM nail is hammered into the canal of a fractured long bone in order to fixate the fractured ends together. The proximal locking is performed first and is usually carried out with a jig. Nail deformation during intramedullary insertion, however, may make a jig inaccurate for the distal screws. The primary difficulty lies in the positioning of the distal locking screws and alignment of the drill for the drilling of the distal screw holes because it is the most time consuming and challenging step of the overall implantation procedure. Consequently, the two main reasons for failure in distal locking are incorrect entry point on the bone and wrong orientation of the drill. If either of these two factors is wrong, then the drill will not go through the nail hole.

An inaccurate entry point also compounds the problem as the rounded end of the drill bit often slips, and it is then difficult to place another drill hole next to the earlier one. Inaccurate distal locking leads to premature failure with breakage of the nail through the nail hole, breakage of the screw or the breaking of the drill bit within the bone.

Manual techniques are the most common and accepted techniques for sighting the distal screw holes and predominate the orthopaedic engineering industry. The majority of distal targeting techniques employ a bushing (cylindrical sleeve) that guides the drill. The mechanism of aligning the guide bushing and keeping it in place differs. There are cases where the surgeons use a half sleeve (bushing cut in half longitudinally) to help steady the drill bit during drilling. In either situation, the surgeon will incise the patient and insert the drill through the incision. The manual techniques are based primarily on the surgeon's manual skill and make use of radiographic x-ray imaging and mechanical jigs. Less common approaches for distal screw positioning and drill alignment is the use of electromagnetic components and lasers.

There remains a need in the art for a system and method for targeting landmarks of an instrumented medical implant. Further, there remains a need in the art for accurately positioning the distal locking screws and aligning the drill for the drilling of the distal screw holes. Further, there remains a need in the art for an instrumented intramedullary nail for the targeting of distal screw holes.

SUMMARY OF THE INVENTION

In one aspect of the invention, there is provided a system for targeting a landmark. The system includes an instrumented medical implant, a control circuit, a power supply, and a landmark identifier. The instrumented medical implant has one or more landmarks and each landmark has a corresponding coil. The control circuit is electrically connected to the corresponding coil, and the power supply is electrically connected to the control circuit. The landmark identifier has a magnetic sensor for sensing the corresponding coil.

In some embodiments, the instrumented medical implant further includes at least one other landmark.

In one particular embodiment, the landmark is an opening.

The instrumented medical implant may be any number of devices. As examples, the instrumented medical implant may be a bone plate, a bone screw, a bone peg, a bone staple, an intramedullary nail, an intramedullary nail cap, an intramedullary nail and plate combination, an interference screw, a hip replacement stem, a hip replacement femoral neck, a hip replacement femoral head, a hip replacement acetabular liner, a hip replacement acetabular shell, a knee replacement tibial tray, a knee replacement tibial tray liner, a knee replacement femoral component, a knee replacement tibial tray shaft extension, a knee replacement patellar implant, a knee replacement wedge, a trochlear groove implant, a femoral canal restrictor, a shoulder replacement humeral stem, a shoulder replacement glenoid component, a shoulder replacement humeral head, an elbow replacement humeral component, an elbow replacement radial component, an elbow replacement ulnar component, an ankle replacement tibial component, or an ankle replacement talar component.

In one particular embodiment, the instrumented orthopaedic implant is an intramedullary nail.

In one embodiment, the control circuit is an oscillator.

In yet another embodiment, the control circuit is a multiplexer.

In some embodiments, the power supply and control circuit are formed of a single unit.

The power supply may be any number of devices. As examples, the power supply may be a capacitor, an inductive coupling, a battery, a mechanically driven power generation unit, a piezoelectric device, or an energy scavenging device. In one particular embodiment, the power supply is an electromagnetic field generating coil.

The landmark identifier may be any number of devices. As examples, the landmark identifier may be a drill guide, a drill sleeve, a drill, a drill nose, a drill barrel, a drill chuck, or a fixation element.

The magnetic sensor may be any number of sensors. As examples, the magnetic sensor may be a Hall effect sensor, a fluxgate magnetic field sensor, an inductive coil sensor, or a magneto-resistive sensor.

In some embodiments, the instrumented medical implant further includes at least one other corresponding coil. In one embodiment, the at least one other corresponding coil is generally orthogonal to the corresponding coil. In yet another embodiment, a relationship between the at least one other corresponding coil and the corresponding coil is selected from the group consisting of generally oblique, offset, coplanar, parallel, collinear, and transverse.

In yet another aspect of the invention, there is provided a method of targeting a landmark relative to an instrumented orthopaedic implant. The method includes the steps of: (a) installing an instrumented orthopaedic implant relative to a bone, the instrumented orthopaedic implant having at least one landmark and at least one corresponding coil proximate to the at least one landmark; (b) energizing the at least one corresponding coil; (c) orienting a landmark identifier relative to the energized at least one corresponding coil; (d) sensing the energized at least one corresponding coil; (e)

processing the sensed at least one corresponding coil data to detect proximity of the landmark identifier relative to the energized at least one corresponding coil; and (f) providing a user with feedback information on the proximity of the landmark identifier relative to the energized at least one corresponding coil.

In some embodiments, the landmark is provided on the instrumented orthopaedic implant.

In some embodiments, the method further includes the step of placing a member through the bone and the instrumented orthopaedic implant. The member may be any number of devices. As examples, the member may be a drill, a tap, a screw, a peg, a pin, a staple, a wire, a provisional fixation device, a bar, a brad, a dowel, a fastener, a pipe, a rivet, a rod, a skewer, a sliding bar, a spike, a stake, a staple, or a stud.

In one embodiment, the method further includes the step of manually securing a portion of the instrumented orthopaedic implant.

In another embodiment, the method further includes the step of securing a portion of the implant using an instrument to aid in landmark identification.

In yet another embodiment, the method further includes the step of energizing at least one other corresponding coil.

In some embodiments, the step of energizing the at least one corresponding coil includes the step of passively energizing the at least one corresponding coil. This may include coupling the at least one corresponding coil with an inductive power source.

In some embodiments, the step of energizing the at least one corresponding coil comprises the step of actively energizing the at least one corresponding coil.

In one embodiment, the method further includes the step of recording sensed data.

In another embodiment, the method further includes the step of emitting a magnetic field from the at least one corresponding coil.

In another embodiment, the step of sensing the energized at least one corresponding coil includes the step of monitoring field intensity of the energized at least one corresponding coil.

In still another embodiment, the method includes the steps of re-orienting the landmark identifier from a first position to a second position and comparing field intensity of the energized at least one corresponding coil between the first position and the second position.

In yet another embodiment, the landmark identifier identifies the largest field intensity.

In still another embodiment, the landmark identifier determines whether the field intensity at least meets a predetermined field intensity threshold.

In one particular embodiment, the feedback information provided is selected from the group consisting of audible, visual, and tactile. The audible feedback may be output through a speaker, headphones, ear buds, or an ear piece. The audible feedback signal may be transmitted over wire or wirelessly using radio frequency or terrestrial data transmission. The visual feedback may be output through a cathode ray tube, a liquid crystal display, or a plasma display. Visual feedback devices may include, as examples, a television monitor, a personal digital assistant, or a personal media player. The visual feedback signal may be transmitted over wire or wirelessly using radio frequency or terrestrial data transmission. The tactile feedback may be output through gloves, instruments, or a floor mat. The tactile feedback signal may be transmitted over wire or wirelessly using radio frequency or terrestrial data transmission.

In yet another embodiment, the method includes the steps of drilling an opening and installing a fastener through the drilled opening.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings.

DETAILED DESCRIPTION OF THE EMBODIMENTS

Figure 1:
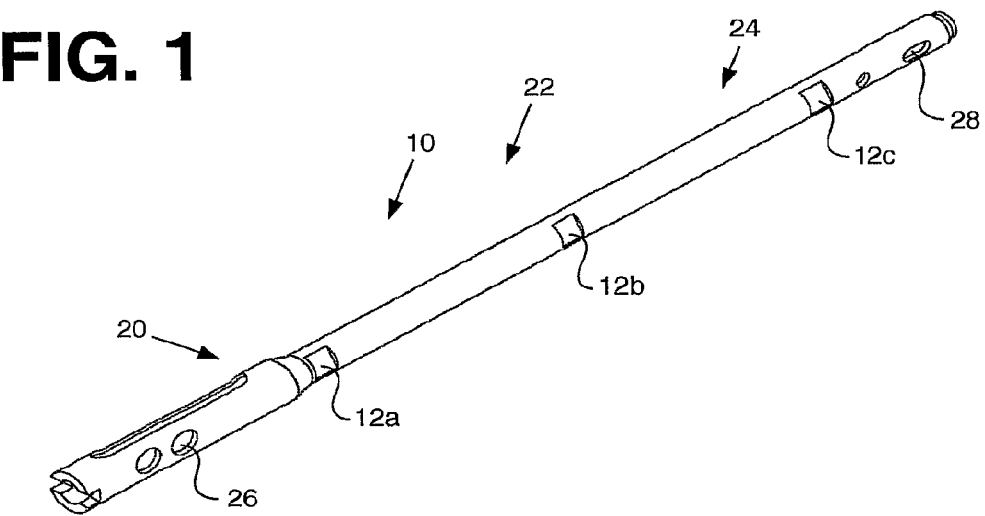
FIG. 1 is a perspective view of a telemetric orthopaedic implant in a first embodiment.
Figure 2:
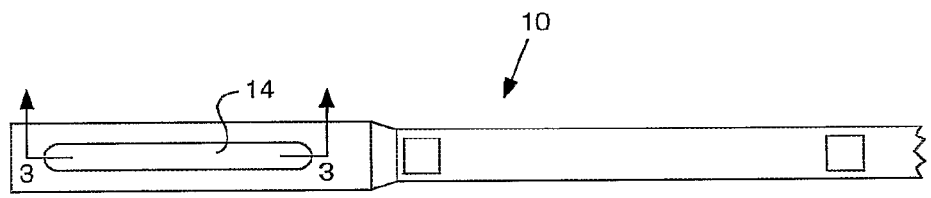
FIG. 2 is a top view of the implant shown in FIG. 1.
Figure 3:
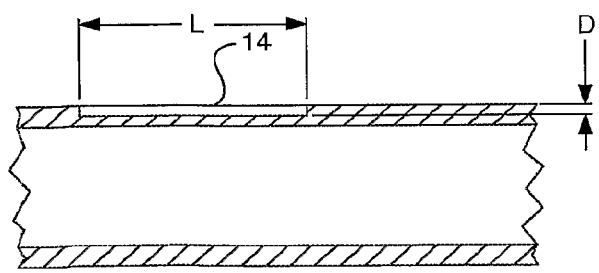
FIG. 3 is a partial sectional side view of the implant shown in FIG. 1.
Figure 4:
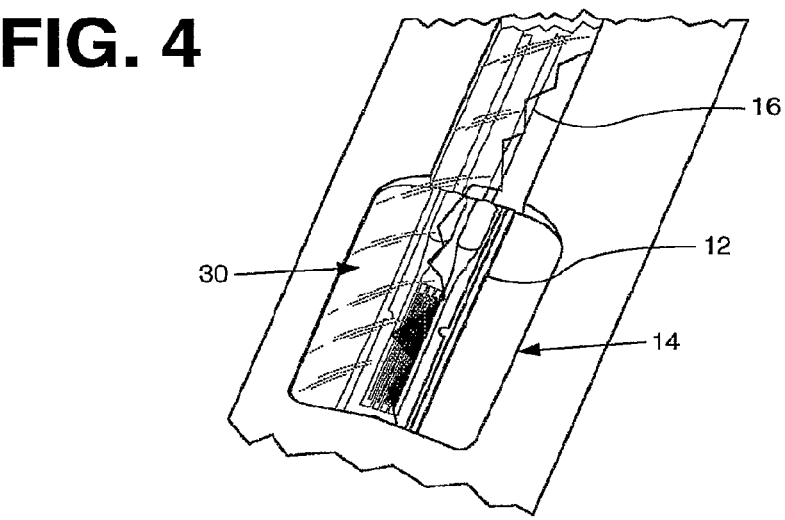
FIG. 4 is a detailed perspective view of the implant shown in FIG. 1.

The following description of the preferred embodiment(s) is merely exemplary in nature and is in no way intended to limit the invention, its application, or uses.

A "smart implant" is an implant that is able to sense its environment, apply intelligence to determine whether action is required, and act on the sensed information to change something in a controlled, beneficial manner. One attractive application of smart implant technology is to measure loads on an orthopaedic implant. For example, an intramedullary nail is subjected to three types of loading: bending, torsional, and compression. These loads may be measured indirectly by measuring sensor output of a series of strain gauges mounted to the orthopaedic implant. In the case of an intramedullary nail, diametrically apposed strain gauges mounted on the outer surfaces of the nail are subjected to tensile and compressive forces, respectively. Typically, the strain measured from the sensors is higher when the implant is loaded in bending than in compression.

A fundamental parameter of the strain gauge is its sensitivity to strain, expressed quantitatively as the gauge factor (G). Gauge factor is defined as the ratio of fractional change in electrical resistance to the fractional change in length (strain), $$G = \frac{\Delta R}{R\varepsilon}, \quad (1)$$

where R=nominal resistance, ΔR=resulting change in resistance and ε=strain. This change in resistance arises from two important factors: (a) the change in the resistivity of the material, and (b) the change in the physical dimensions of the resistor as the material is deformed. For a foil strain gauge, G is found to be 2.1. Voltage recordings are converted to strain using the following equation:—

$$\varepsilon = \frac{-4V_r}{GF(1+2V_r)} \times \left(1 + \frac{R_L}{R_g}\right), \quad (2)$$

where RL is the lead resistance, Rg is the nominal gauge resistance, which is specified by the gauge manufacturer, GF is the Gauge Factor, which is also specified by the gauge manufacturer, and Vr is the voltage ratio defined by the following equation:—

$$V_r = \left(\frac{V_{CH}(\text{strained}) - V_{CH}(\text{unstrained})}{V_{EX}}\right), \quad (3)$$

where VCH and VEX are the measured signal's voltage and excitation voltage respectively. Strain is related to stress using Hooke's Law which can be rearranged to calculate the compression and bending loads experienced by the implant (F), $$F = E \cdot \varepsilon \cdot A, \quad (4)$$

where E is the stiffness of the implant in gigapascals (GPa), ε=strain measured from the output of the instrumented implant, and A is the cross-sectional area of the implant in square meters (m$^2$). The corresponding load on the bone is deduced by subtracting the implant load from the total downward force exerted by the limb measured using either a force plate or a balance.

Incorporation of sensors and other electronic components within an implantable medical device, such as an intramedullary nail, alters its primary function from a passive load-supporting device to a smart "intelligent" system with the ability to record and monitor patient activity and compliance.

Telemetric Intramedullary Nail

Referring to the accompanying drawings in which like reference numbers indicate like elements, FIG. 1 illustrates a telemetric intramedullary (IM) nail 10. The telemetric IM nail 10 includes at least one sensor 12. One particular sensor configuration is illustrated in FIG. 1. In this embodiment, sensors 12 are located in a proximal region 20, a central or mid-shaft region 22, and a distal region 24 of the IM nail 10. In the embodiment depicted in FIG. 1, the telemetric IM nail 10 includes three sensors 12a, 12b, 12c with a sensor corresponding to each region. However, those of ordinary skill in the art would understand that a greater or lesser number of sensors may be used and that sensors may be applied in other configurations. The telemetric nail 10 continuously measures a set of strain values generated from the sensors 12. As explained in greater detail below, the telemetric IM nail 10 transmits the measurements from the nail to a reader device for calculation of the forces components without disturbing fracture healing.

The telemetric IM nail 10 may include features to allow fixation of the nail to bone. For example, the telemetric IM nail 10 may include proximal apertures 26 and/or distal apertures 28. In the embodiment depicted in FIG. 1, the telemetric IM nail 10 includes two proximal holes 26, a distal hole 28, and a distal slot 28, but those of ordinary skill in the art would understand that a greater or lesser number of apertures may be provided.

Figure 5:
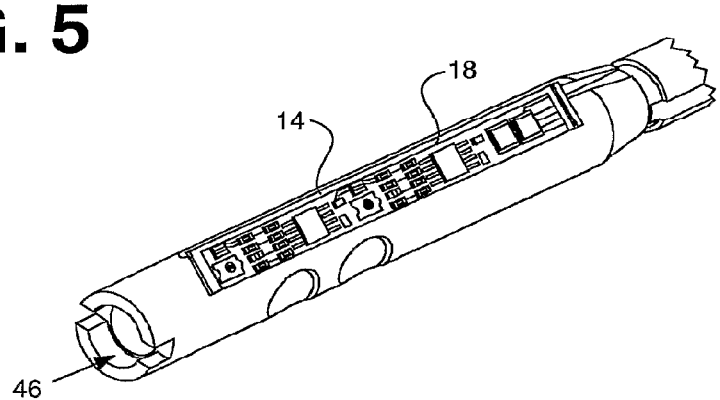
FIG. 5 is a perspective view of a telemetric orthopaedic implant in a second embodiment.

As best seen in FIG. 5, the telemetric IM nail 10 also includes one or more electronic components 18, such as a printed circuit board. The electronic components 18 form an instrumentation circuit with the sensors 12. The electronic components 18 may include associated signal conditioning circuitry, one or more microprocessors, one or more memory devices, a power supply, and communications components. The electronic components 18 allow in situ measurement of changes in the local environment. The combination of the sensor 12 and the electronic components 18 provide a powerful tool for indirect measurement of the changing load over time due to fracture consolidation using the algorithm described above. In turn, these indirect measurements may be used to provide information to clinicians on the environment for use in clinical decision making.

In order to maintain the integrity of the telemetric IM nail 10, the implant design must protect the components, provide an accurate and stable connection between the sensor and its environment, and maintain the functionality of the implant itself. Incorporating sensors within the structure of internal implants raises the "packaging problem" of maintaining the insulation of electronics, as biological tissues are an extremely hostile environment. Furthermore, the risk of damage to the electronic components 18 from common sterilization methods cannot be underestimated. Design considerations for instrumenting the IM nail 10 requires minimization of any damage to the mechanical and physical properties of the nail and allow for large scale commercialization and manufacture. Certain designs may be confirmed by measuring the bending stiffness and fatigue behavior of the IM nail 10 before and after instrumentation.

As best seen in FIGS. 2-5, the IM nail 10 includes at least one recess 14. As examples, the recess 14 may be rectangular, square, circular, elliptical, or some combination thereof. The recess 14 may be made using various manufacturing techniques including, but not limited to machining, milling, grinding, forging, casting, stamping, and injection molding. The recess 14 has a depth D, which ranges from about 0.1 mm to about 9.0 mm. The length L of the recess may be in the range from about 1 mm to about 100 mm. In the embodiment depicted in FIG. 3, the recess 14 is about 0.5 mm thick and about 5 mm long. The recess 14 receives the sensor 12 and conductor wires 16. The recess 14 protects the sensor 12 and conductor wires 16 from abrasive damage during the surgical insertion process. The recess 14 is located on either an anterior surface or a posterior surface enabling the sensors 12 to experience tensile and compression forces respectively. The sensor 12 may be fixed in the recess 14 using a range of high stiffness adhesives including epoxy resins, polyurethanes, UV curable adhesives, and medical grade cyanoacrylates. These types of fixation methods do not adversely affect the performance of the sensor 12.

Additionally, the telemetric IM nail 10 may include a recess 14 in the proximal region 20 to receive the electronic components 18. The recess 14 is dimensioned to accept the electronic components 18. For example, the electronic components may be about 56 mm long, about 6.2 mm wide, and about 0.25 mm thick, and the recess 14 is sized accordingly. The recess 14 may be of the same size as the electronic components 18 or slightly larger.

Alternatively, installation of the strain gauges 12 and other electronic components may be carried out using a more evasive method, such as electro-discharge milling a longitudinal section in the implant, installing the components in the IM nail 10, and laser welding the tube segments. However, there are several disadvantages to using this approach. Localized heat of welding tends to cause distortion and warping of the base metals or stresses around the weld area, which could affect the corrosion resistance of the implant. Moreover, laser beam welding has a tremendous temperature differential between the molten metal and the base metal immediately adjacent to the weld. Heating and cooling rates are much higher in laser beam welding than in arc welding, and the heat-affected zones are much smaller. Rapid cooling rates can create problems such as cracking in high carbon steels.

There are a number of ways to encapsulate the sensors 12 and other electronic components. Some components may require more durable methods of encapsulation than others. For example, if a battery or other potentially hazardous device is included in the electronics system a titanium case may be required. Alternatively, if the components are biologically benign, then a simple potting material, such as polyurethane or a silicone, may prove to be sufficient. Those skilled in the art would understand that various materials may be used for the potting material. What is significant is that the potting material acts as a cover to separate the electronic components from the surrounding environment. Soldering and welding techniques may also be used to help permanently seal the sensors 12 and other electronic components inside the instrumented nail 10. Substituting the standard foil gauge with platinum strain gauges may also enhance durability and resistance to sterilization and attack by biological fluids.

Figure 6:
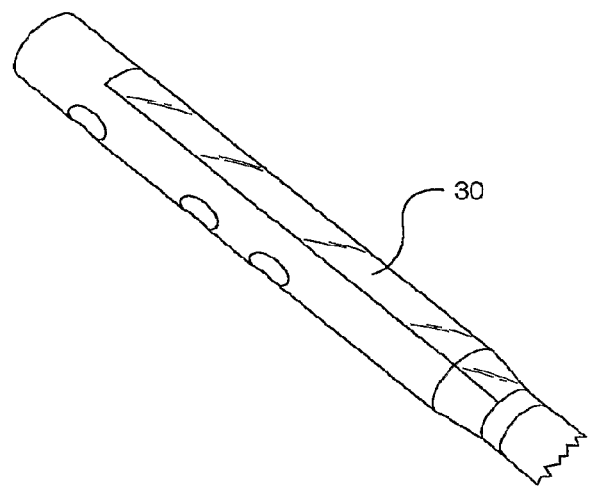
FIG. 6 is a perspective view of the telemetric orthopaedic implant shown in FIG. 5.

In one particular embodiment in FIG. 6, the sensors 12 and the electronic components 18 are covered with a biocompatible potting material 30, such as polyurethane or silicone, in order to provide a hermetic seal. Because the sensors 12 and the electronic components 18 are sealed hermetically from the patient tissues and fluids, long term function of the telemetric IM nail 10 is achievable. At the same time, leakage of non-biocompatible or toxic materials is eliminated. The potting material 30 is an electrically insulative, moisture resistant material, supplied in either a liquid or putty-like form and is used as a protective coating on sensitive areas of electrical and electronic equipment. The potting material 30 may be optically opaque or colorless. The strain gauges 12 and conductor wires 16 are covered in potting material 30 with suitable mechanical characteristics required to survive the implantation process and restore the mechanical envelope.

Figure 7:
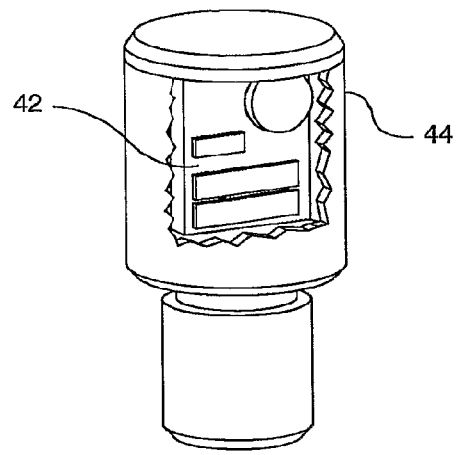
FIG. 7 is a perspective view of an insert.
Figure 8:
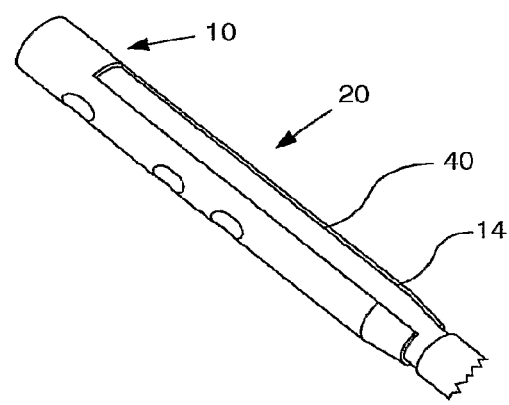
FIG. 8 is a perspective view of a telemetric orthopaedic implant in a third embodiment.
Figure 9:
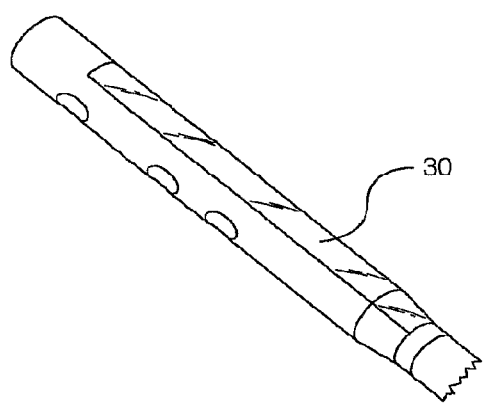
FIG. 9 is a perspective view of the telemetric orthopaedic implant shown in FIG. 8.

An alternative arrangement of the electronic components 18 in the telemetric instrumented nail 10 is shown in FIGS. 7, 8, and 9. In this particular design, passive electronic components 40 are located in the recess 14 of the proximal region 20 and active electronic components 42, such as a power supply, microprocessor, data storage device, and external communication device, are contained in a separate nail head insert 44. As best seen in FIG. 9, the passive electronic components 40 may be covered with the potting material 30 to hermetically seal the electronic components 40. In this configuration, the telemetric IM nail 10 is implanted in the usual manner, and, once the nail has been implanted into the bone, the nail head insert 44 is attached to the telemetric IM nail 10. For example, the nail head insert 44 may be threaded into a hole 46 (best seen in FIG. 5). This particular design avoids any sensitive electronics being damaged by the implantation process. Connections between the passive and active electronic components 40, 42 are made using either an inductively coupled link or physical connections via slip rings.

The telemetric IM nail 10 may be constructed from a biocompatible material using standard manufacturing techniques. For example, the nail may be forged out of metal, hand or machine laid composite, or machined from stock. Alternatively, the telemetric IM nail 10 may be cast, injection molded, or compacted through hot isostatic processing (HIP). The HIP manufacturing process is particularly suited for producing nails with preformed recesses designed to receive sensors and electronic components.

In yet another alternative embodiment, the telemetric IM nail 10 may be constructed using a biodegradable composite whose degradation rate is controlled by sensed strain data. Such a device is more compliant than a conventional metal implant because the mechanical modulus of the implant changes according to the degree of healing of the adjacent bone. Increased load bearing capacity on the healing bone triggers the release of an active agent that accelerates the degradation rate of the nail in order to reduce its load sharing ability. On the other hand, slow healers require the release of active agents that inhibit the degradation rate of the implant material. The release of the active agent may be controlled using a micro-electromechanical structures (MEMS) reservoir system that releases a chemical manipulation on demand that either accelerates or decelerates the rate of degradation of the nail. The instrumented components may be manufactured using restorable materials, such as degradable, porous silicon wafers. Otherwise, non-degradable electronic components may remain in the patient, which may be acceptable in some cases.

Figure 10:
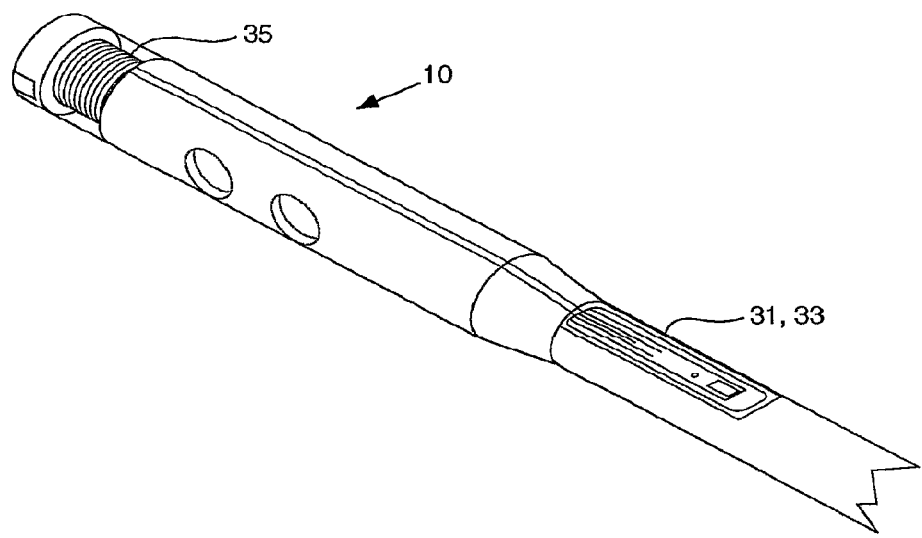
FIG. 10 is a perspective view of a telemetric orthopaedic implant in a fourth embodiment.
Figure 11:
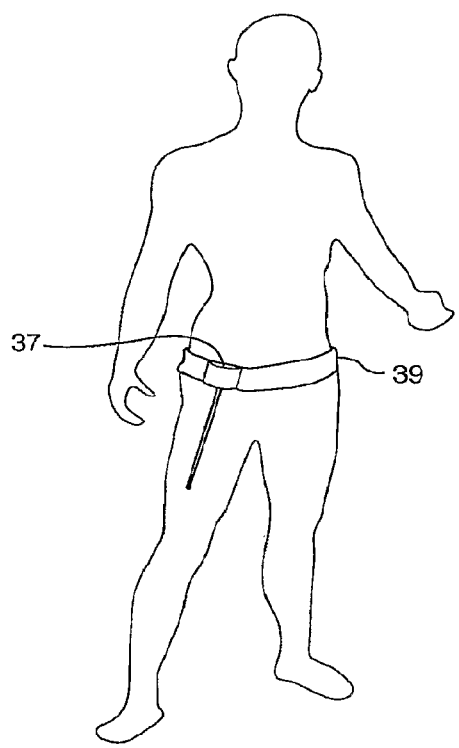
FIG. 11 is a perspective view of an external reader as mounted on a belt.

FIGS. 10 and 11 illustrate one particular embodiment of the telemetric IM nail 10. The telemetric IM nail 10 includes a single foil strain gauge 31, a printed circuit board 33, and a driver coil 35. In some embodiments, the printed circuit board 33 includes a microprocessor (not shown) and an oscillator (not shown). At least some of these components may be placed within a machined cavity located on the telemetric IM nail 10 and covered with a biocompatible potting material. In the depicted embodiment, the telemetric IM nail 10 is a femoral antegrade nail and the strain gauge is located on the anterior "tensile loaded" surface of the nail. The telemetric IM nail 10 may include a low power telemetry system that is only activated when the telemetric IM nail 10 is within an interrogation zone of an external reader or interrogator 37. The transmission of power across an air gap is achieved using magnetic fields generated by inductive couple power transfer. The air gap is in the range of about 30 mm to about 110 mm, with a particularly suitable range from about 60 mm to about 80 mm. The strain gauge produces a measurable effect in the reader coil from which strain can be determined. When the telemetric IM nail 10 is not being read, it is in "sleep" mode.

As best seen in FIG. 11, the interrogator 37 is a belt 39 worn by the subject around the waist during data acquisition. The belt 39 may be worn at the subject's residence or at a clinic or other healthcare facility. The data may be transmitted by wire or wirelessly to a computing device, such as a personal computer, laptop, personal data assistant, or the like.

As an example of use, the telemetric IM nail 10 and the belt may be used to capture strain data. By analyzing the data, a user can determine the healing status or progression of the subject. The data may include, as an example only, the maximum strain recorded over a period of time, such as several months. The entire healing period may be six months or more depending upon the healing progression of the subject. In the case of the strain gauge, the load component of the healing bone can be determined by subtracting the implant load from the total load measured in the operated limb. The strain rate measurements may be used to estimate the degree of healing. Moreover, the strain rate measurements may provide insight into the stiffness of the healing bone for various activity levels specific to the subject and type of injury. The inductive couple power transfer enables the healing status of the implant to be monitored for the entire lifetime of the subject. Thus, the user may look many years later for changes in the implant as a result of old-age, trauma, or disease. While the depicted embodiments relate to intramedullary nails, those of ordinary skill in the art would understand that the invention is also well suited for joint replacement applications.

FE Modeling to Determine Optimum Position of Sensors

Figure 12:
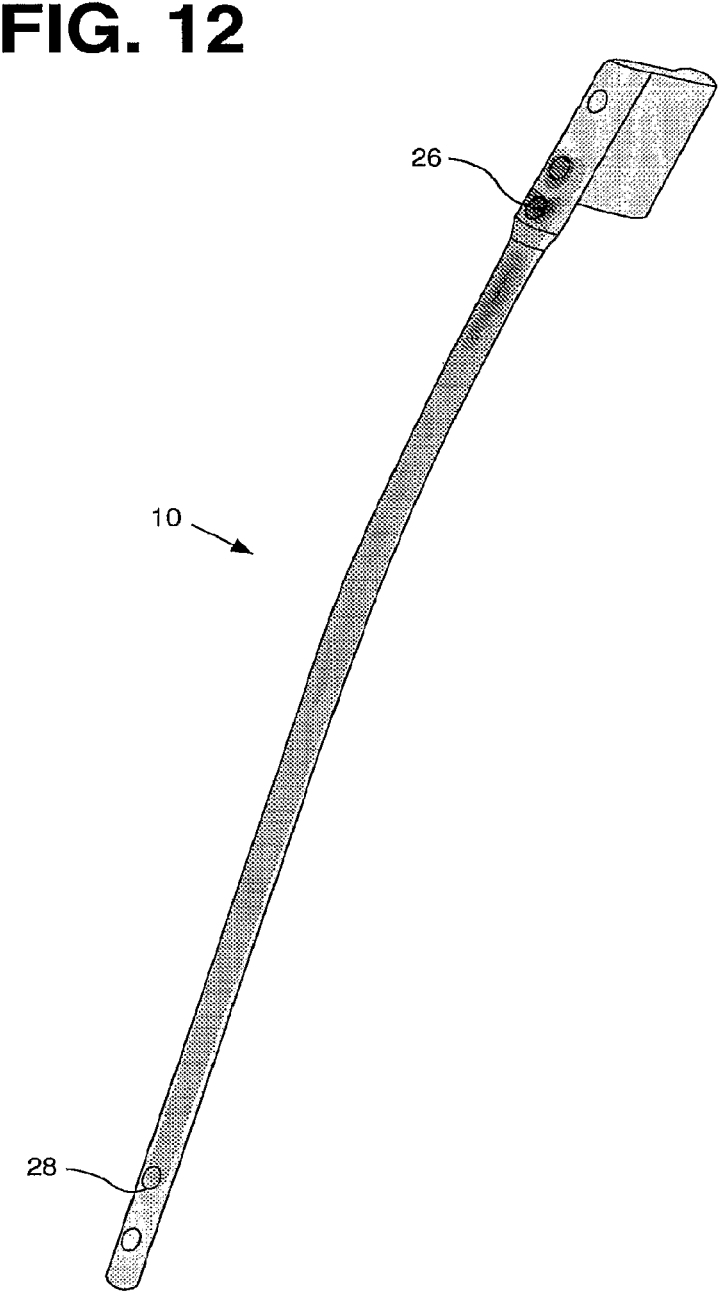
FIG. 12 is a perspective view of a telemetric orthopaedic implant illustrating the results of finite element analysis.

Referring now to FIG. 12, the sensors 12 may be devices capable of measuring mechanical strain, such as foil or semi-conductor strain gauges. Alternatively, the sensors 12 may be load cells used to directly measure mechanical load. The embodiment depicted in FIG. 1 utilizes foil strain gauges to measure strain. The optimum location of the sensors 12 for the purpose of measuring strain may be determined through finite element (FE) analysis. The sensors 12 may be located, for example, but not limited to, in the working region of the implant 10. The working region is defined as the region between two fixation apertures 26, 28. The fixation apertures 26, 28 are adapted to receive fasteners, such as screws, to attach the implant 10 to bone. As can be seen in FIG. 10, the darker, shaded areas represent stress concentrations. The stress distribution results from the way in which the nail 10 is loaded through the patient's hip joint and results in high bending stresses on the outer surface of the nail 10, aligned with the proximal apertures 26. Typically, a 50% reduction in stress is observed between sensors placed inside the implant as opposed to an external mounting.

Sensor

The telemetric IM nail 10 includes the sensor 12. The sensor 12 senses at least one item, event, condition, etc. The sensor 12 may be any number of types including, but not limited to, a foil strain gauge, a semi-conductor strain gauge, a vibrating beam sensor, a force sensor, a piezoelectric element, a fiber Bragg grating, a gyrocompass, or a giant magneto-impedance (GMI) sensor. Further, the sensor 12 may indicate any kind of condition including, but not limited to, strain, pH, temperature, pressure, displacement, flow, acceleration, direction, acoustic emissions, voltage, pulse, biomarker indications, such as a specific protein indications, chemical presence, such as by an oxygen detector, by an oxygen potential detector, or by a carbon dioxide detector, a metabolic activity, or biologic indications to indicate the presence of white blood cells, red blood cell, platelets, osteoblasts, osteoclasts, growth factors, or collagens. Finally, the sensor 12 may be an image capturing device.

Some orthopaedic applications may require more than one sensor to measure more than one item, event, or condition. Thus, some implants require multi-channel capabilities. For example, the telemetric IM nail 10 may include six or more strain gauges. The sensor 12 may be an array of sensors or a series of discrete sensors. The telemetric IM nail 10 also may be designed with multi-axial strain gauges in a rosette configuration to allow for the measurement of loads in x, y and/or z planes. The configuration of the sensors 12 also may be tailored to meet the requirements of the patients fracture. The sensor 12 is designed in such way that it does not compromise the performance of the implant. For example, the sensor 12 must be unobtrusive, biocompatible, and in no way affect the established biomechanical performance of the implant. It has been shown that nails with a tight fit between implant and the adjacent bone may be deformed significantly during insertion. As a result, the resolution of the selected sensor is better than 8 bit (0.05%). The output of the sensor may be investigated by applying an axial load to the instrumented nail.

Figure 13:
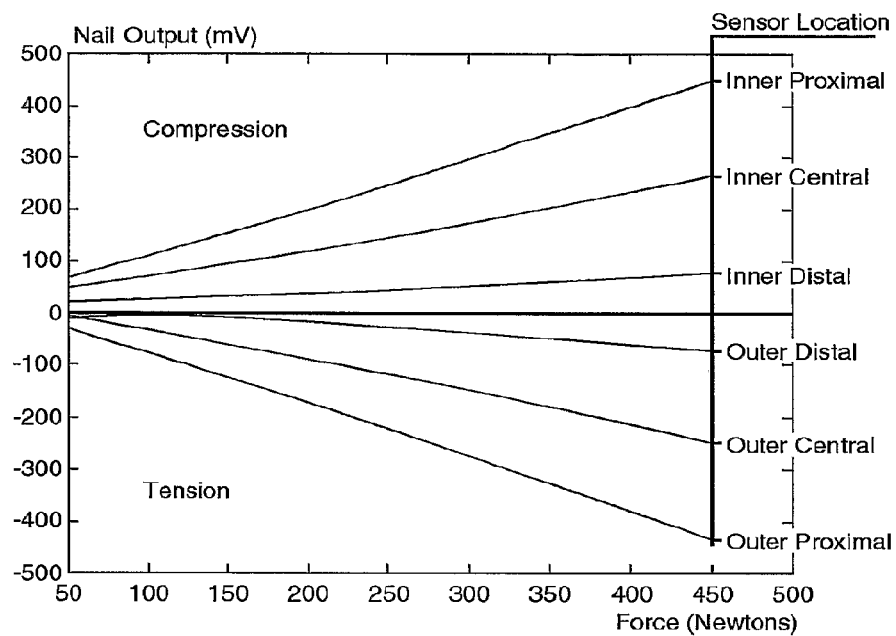
FIG. 13 is a graph illustrating data output vs. force.

The loading configuration is designed to match the loading pattern typically observed in a human femur, i.e. an offset vertical load transmitted through the nail via the proximal fastener. Strain vs. load plots for three instrumented IM nails with two strain sensors 12 located on the inner (compression) and outer (tensile) surfaces at either the mid-shaft region (nail 1), distal region (nail 2), or proximal region (nail 3) respectively are shown in FIG. 13. In all cases, the responses from the sensor pairs are fairly linear when the load on the nail is ramped up to 500 N. In addition, there is little or no hysteresis observed when the load is applied and removed from the nail.

As noted above, the sensor 12 may be an accelerometer, obtaining nearly continuous changes in acceleration over time at a sampling rate from about 0.5 Hz to about 20000 Hz. The system also may be designed with multi-axial accelerometers in varying configurations to enable changes in acceleration measurement in x, y and z planes. The accelerometer embedded into the IM is designed in such way that it does not compromise the performance of the implant, i.e. unobtrusive, biocompatible, and in no way affect the established biomechanical performance.

The sensors may be any combination of devices capable of measuring raw acceleration or change in relative acceleration of the implant, patient extremity, any portion of the patient's body, cast, brace, splint, or boot. In the current invention the sensor could be MEMS (micro-electromechanical system) or non-MEMS based accelerometer in a cantilever beam configuration or other relevant configuration (spring-mass-damper), gravimeter, vibrating beam, and/or gyroscope. The sensor could be analog or digital with any numbers of axes including a maximum swing of ±50 g. The sensitivity of the sensor is sufficient to capture the acceleration data such that when amplified the data is recognizable and discernable (e.g. 0.0001-100 mV/g). The sensor bandwidth is suitable to ensure proper data generation and capture (e.g. 0.01-20000 Hz). Further, the operating temperature of the sensor allows for implantation as well as ambient conditions if the sensor is being worn. An acceptable operating temperature range is −50-150 degrees F.

Communication

The electronic components 18 are in communication with a data receiver 50. The electronic components 18 receive data from the sensor 12 and transmit the data to the data receiver 50. The electronic components 18 transmit the data by wire or through a wireless connection. The transmission may use available technologies, such as ZIGBEE™, BLUETOOTH™, Matrix technology developed by The Technology Partnership Plc. (TTP), or other Radio Frequency (RF) technology. ZigBee is a published specification set of high level communication protocols designed for wireless personal area networks (WPANs). The ZIGBEE trademark is owned by ZigBee Alliance Corp., 2400 Camino Ramon, Suite 375, San Ramon, Calif., U.S.A. 94583. Bluetooth is a technical industry standard that facilitates short range communication between wireless devices. The BLUETOOTH trademark is owned by Bluetooth Sig, Inc., 500 108th Avenue NE, Suite 250, Bellevue Wash., U.S.A. 98004. RF is a wireless communication technology using electromagnetic waves to transmit and receive data using a signal above approximately 0.1 MHz in frequency. Due to size and power consumption constraints, the telemetric IM nail 10 may utilize the Medical Implantable Communications Service (MICS) in order to meet certain international standards for communication.

Instrumentation System

Figure 14:
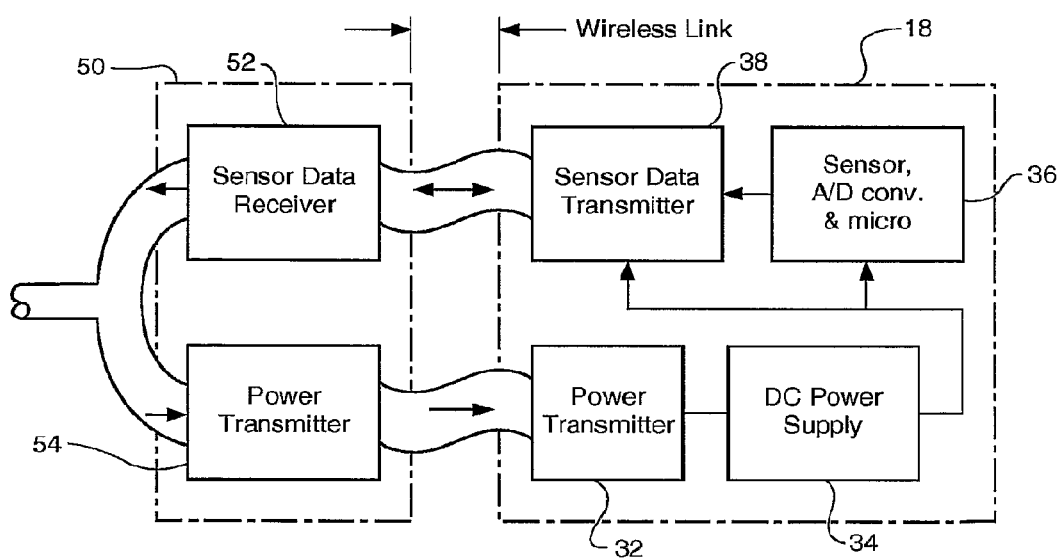
FIG. 14 is a schematic illustrating an electronic component and a data receiver.

FIG. 14 illustrates the electronic components 18, such as a printed circuit board, and the data receiver 50. The electronic component 18 includes a power transmitter 32, a DC power supply 34, a combination analog/digital converter and microprocessor 36, and a sensor data transmitter 38. The data receiver 50 includes a sensor data receiver 52 and a power transmitter 54. Although illustrated as separate components, those of ordinary skill in the art would understand that the transmitter and the receiver may be combined in a single unit, sometimes referred to as a transceiver. In the embodiment depicted in FIG. 14, power consumption and data transmission are contactless. The electronic component 18 may include any of the following: (1) any number of foil strain gauges; (2) matching number of low noise, low power instrumentation amplifiers; (3) matching number of Wheatstone bridge resistor networks; (4) matching number of strain gauge zero-adjustments; and (5) on-board power supply with noise filtering.

One particular arrangement of the system architecture is illustrated in FIG. 14. In this particular example, power consumption and data transmission are contactless.

The circuitry is designed to fit within the nail and provide either a wired or wireless interface with the onboard sensors, and allow low-noise measurements.

Power Management

The telemetric IM nail 10 may incorporate one or more power management strategies. Power management strategies may include implanted power sources or inductive power sources. Implanted power sources may be something simple, such as a battery, or something more complex, such as energy scavenging devices. Energy scavenging devices may include motion powered piezoelectric or electromagnetic generators and associated charge storage devices. Inductive power sources include inductive coupling systems and Radio Frequency (RF) electromagnetic fields.

Finally, the telemetric IM nail 10 may incorporate a storage device (not shown). The storage device may be charged by an inductive/RF coupling or by an internal energy scavenging device. The storage device must have sufficient capacity to store enough energy at least to perform a single shot measurement and to subsequently process and communicate the result.

Figure 15:
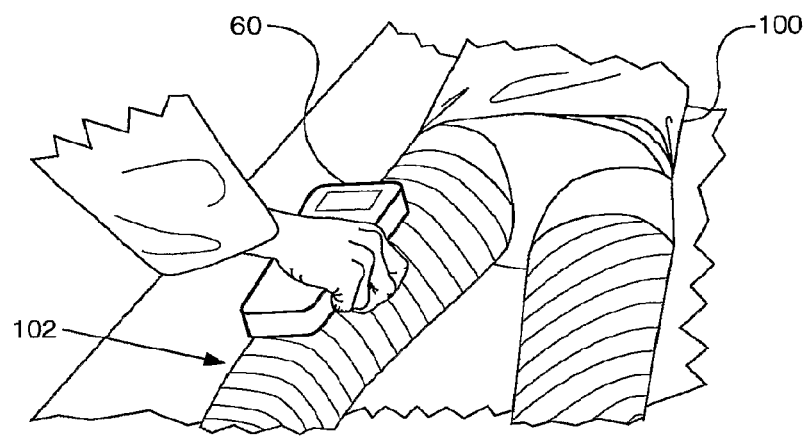
FIG. 15 illustrates use of a handheld device.
Figure 16:
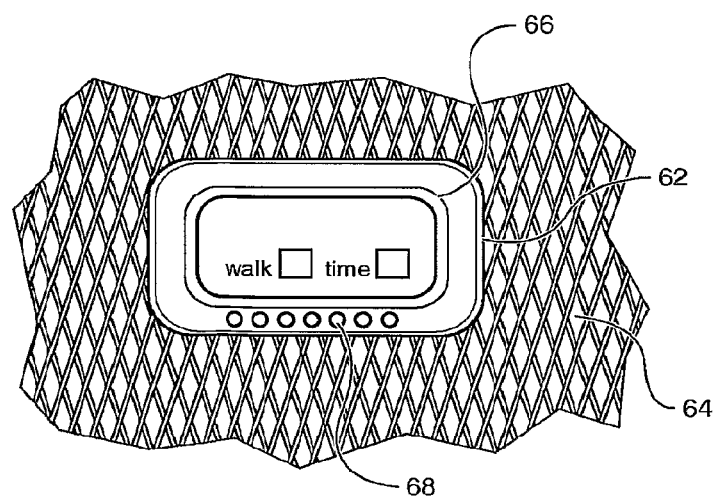
FIG. 16 illustrates a control unit.

FIG. 15 illustrates a handheld device 60 being placed on a leg 102 of a patient 100. The handheld device 60 generates RF waves that excite the electronic component 18. The excited electronic component 18 retrieves stored sensor readings and sends them to the handheld device 60 via a carrier wave. The handheld device 60 may be equipped with a processor (not shown) for direct analysis of the sensor readings or the handheld device 60 may be connected to a computer for analysis of the sensor readings.

Communication

The demands on an implantable telemetry system are severe and robust methods must be utilized to capture data from the orthopaedic implant. Prior attempts in the art have not provided a signal in the range needed for an instrumented intramedullary nail. Thus, the telemetric IM nail 10 has a wired interface in its most simplified version. In other words, the electronic components 18 are connected to an external control unit 62 via a wire (not shown). The control unit 62 may be placed on the patient 100 as a wearable device, such as an arm band, wrist band, thigh band, or anklet bracelet. Alternatively, the control unit 62 may be connected to a cast 64, such as by placing the control unit inside the cast or attaching the control unit to the exterior of the cast.

The control unit 62 may include a display 66 and/or a speaker 68. The display 66 may be used to display sensor readings, provide warning lights, a count down timer allowing the patient to anticipate an important event, such as cast removal, or an entertainment device, such as an electronic game, to occupy time. The speaker 68 may be used to provide sounds, such as pre-recorded instruction, warning sounds, or game sounds.

The patient actively wears the control unit 62 which constantly monitors the patient's activity. In the case of a major event, such as a traumatic incident or loss of essential body function, the control unit 62 senses this change and sends out an alert which could be audible and/or visual. Alternatively or in addition to the alert, the control unit 62 may send information to another device which could prompt the wearer for information to confirm the patient's status. The control unit 62 also could be used to notify emergency assistance groups of impending danger and other pertinent information, such as location of the patient. In this last example, the control unit 62 may include a global positioning system (GPS) module to locate the control unit and patient.

The control unit 62 may be housed in virtually any type of material, such as plastic, rubber, metal, glass, ceramic, wood, stone, long fiber composites, short fiber composites, non-fiber composites, etc. The display 66 may be a liquid crystal display, a light emitting diode display, a plasma display, a digital light processing, a liquid crystal on silicon display, cathode ray tube, etc.

In other embodiments, however, the telemetric IM nail 10 has a wireless communications facility to allow the patient to move around freely. This embodiment is partially depicted in FIG. 14.

In some embodiments, the sensor is a separate entity from the control unit. This sensor is worn or otherwise attached to the outside of the patient's body or integrated in some fashion into the implant. In any case, the control unit could be placed on the body as a wearable device (arm band, wrist band, thigh band, anklet) or placed inside or attached to a plaster cast. Alternatively, the control unit may be an integral part of the implant.

Using an Instrumented Implant to Target a Landmark

Figure 17:
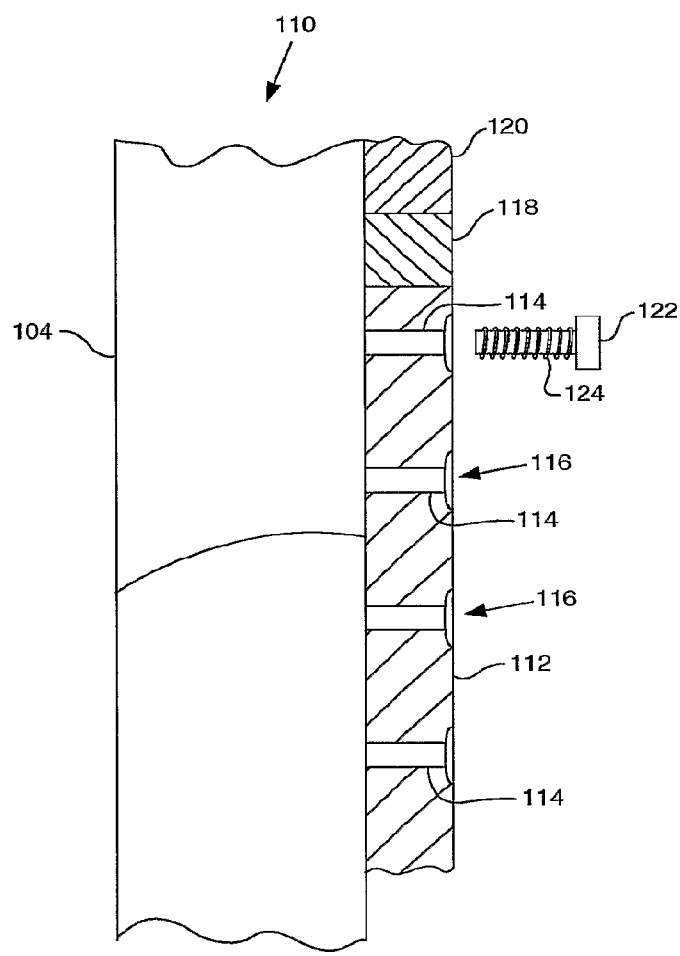
FIG. 17 is a side view of a system for targeting a landmark in a first embodiment.

FIG. 17 illustrates a system 110 for targeting a landmark. The system 110 includes an instrumented medical implant 112, a control circuit 118, a power supply 120, and a landmark identifier 122. The instrumented medical implant 112 has one or more landmarks 114 and each landmark has a corresponding coil 116. The corresponding coil 116 also may be termed an associated coil. In the depicted embodiment, the landmark 114 is an opening, and there are four openings. The control circuit 118 is electrically connected to the corresponding coils 116, and the power supply 120 is electrically connected to the control circuit 118. In some embodiments, the power supply and the control circuit are formed of a single unit. The landmark identifier 122 has a magnetic sensor 124 for sensing the corresponding coils 116. The magnetic sensor 124 may be any number of sensors. As examples, the magnetic sensor may be a Hall effect sensor, a fluxgate magnetic field sensor, an inductive coil sensor, or a magneto-resistive sensor.

The instrumented medical implant may be any number of devices. As examples, the instrumented medical implant may be a bone plate, a bone screw, a bone peg, a bone staple, an intramedullary nail, an intramedullary nail cap, an intramedullary nail and plate combination, an interference screw, a hip replacement stem, a hip replacement femoral neck, a hip replacement femoral head, a hip replacement acetabular liner, a hip replacement acetabular shell, a knee replacement tibial tray, a knee replacement tibial tray liner, a knee replacement femoral component, a knee replacement tibial tray shaft extension, a knee replacement patellar implant, a knee replacement wedge, a trochlear groove implant, a femoral canal restrictor, a shoulder replacement humeral stem, a shoulder replacement glenoid component, a shoulder replacement humeral head, an elbow replacement humeral component, an elbow replacement radial component, an elbow replacement ulnar component, an ankle replacement tibial component, or an ankle replacement talar component. In the depicted embodiment, the instrumented medical implant is a bone plate.

In one embodiment, the control circuit 118 is an oscillator. In yet another embodiment, the control circuit is a multiplexer. The control circuit energizes the corresponding coils. The magnetic sensor 124 senses the field intensity of the pulsating corresponding coils. As is explained in greater detail below, the sensed corresponding coil data is processed to detect the proximity of the landmark identifier relative to the energized corresponding coil, and when the proximity is deemed acceptable, feedback information is provided to a user. The feedback information may take the form of an audible, visual, or tactile signal.

The power supply may be any number of devices. As examples, the power supply may be a capacitor, an inductive coupling, a battery, a mechanically driven power generation unit, a piezoelectric device, or an energy scavenging device.

The landmark identifier may be any number of devices. As examples, the landmark identifier may be a drill guide, a drill sleeve, a drill, a drill nose, a drill barrel, a drill chuck, or a fixation element. In the depicted embodiment, the landmark identifier is a drill sleeve. The landmark identifier may be metal or plastic and may include a coil winding to form the magnetic sensor. In the case of a metal landmark identifier, a portion of the landmark identifier may be coated or covered with an insulating material.

In the embodiment depicted in FIG. 17, the instrumented medical implant further includes four corresponding coils. In one embodiment, the corresponding coils are generally orthogonal to one another. In other embodiments, a relationship between the corresponding coils may be substantially oblique, substantially offset, substantially coplanar, substantially parallel, substantially collinear, or substantially transverse.

Figure 18:
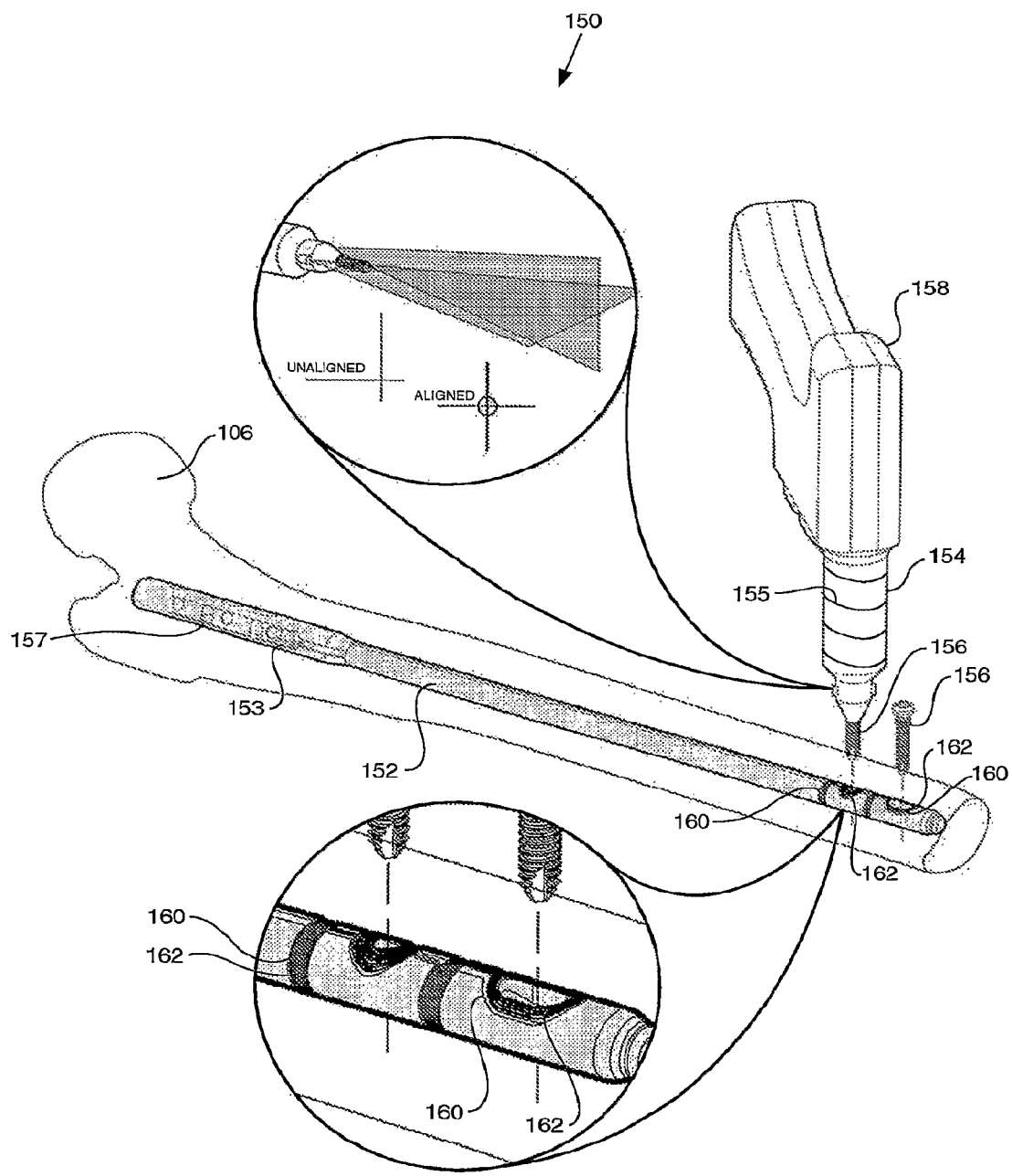
FIG. 18 is a schematic representation of a system for targeting a landmark in a second embodiment.

FIG. 18 illustrates a second embodiment of the system 150 for targeting a landmark. The system 150 includes an instrumented medical implant 152 and a landmark identifier 154. In the depicted embodiment, the instrumented medical implant is an intramedullary nail and the landmark identifier is a drill barrel of a drill 158. The instrumented medical implant may incorporate any of the devices associated with the telemetric nail 10. The instrumented medical implant includes a control circuit 153, a power supply 157, landmarks 160 and corresponding coils 162. In the depicted embodiment, one landmark is a hole and the other is a slot. The system 150 may be used to target fixation elements or fasteners 156 to secure the instrumented medical implant 152 to a bone 106. The landmark identifier 154 includes a magnetic sensor 155. In some embodiments, the landmark identifier 154 includes more than one magnetic sensor 155. The power supply 157 may be an inductive coupling. As is explained in greater detail below, in some embodiments the control circuit 153 and/or the power supply 157 are detachably mounted to the instrumented medical implant 152 through the use of a nail insert.

The landmark identifier 154 and the magnetic sensor 155 transduce the magnetic field generated by the coils 162 into electrical signals. The electrical signals may be displayed as graphical data on a computer, personal device assistant (PDA), or other device capable of showing video. The magnetic sensor 155 may be a Hall effect sensor, a fluxgate sensor, an inductive coil sensor, or a magneto-resistive sensor. The graphical data enables a user to maneuver the landmark identifier until the landmarks 160 are detected. In the depicted embodiment, the drill barrel enables the fasteners 156 to be substantially aligned with the axis of the hole or slot.

In another embodiment, the electrical signal is transduced by additional onboard sensors located on the landmark identifier into a sound signal which alerts the user when the magnetic sensor 155 is generally located over the top of the landmarks 160.

In still another embodiment, the electrical signal is transduced into a visual signal by additional onboard sensors which power either light emitting diodes (LED's) or a laser diode. The LED's illuminate when the magnetic sensor 155 is correctly positioned and oriented over the landmarks 160. Alternatively, the laser diode mounted on the landmark identifier produces a laser crosshair which relay the position of the landmarks to the user. Successful alignment of the cross-hairs informs the user that the landmarks are precisely located.

Power management strategies could include implanted power sources, e.g. batteries or may make use of energy scavenging devices, such as motion powered piezoelectric or electromagnetic generators and associated charge storage devices. Other forms of power supply could include inductively coupled systems or Radio Frequency (RF) electromagnetic fields. It may also be possible to charge a storage device with sufficient energy (either through inductive/RF coupling or internal energy scavenging) to perform a single shot measurement and to subsequently process and communicate the result.

The landmark identifier may be in communication with a computer or personal device assistant either by a hard wire or wireless connection using available technologies, such as Zigbee, Bluetooth or other Radio Frequency (RF) communication. Wireless communication has an advantage over hard wired format because wireless communication has a reduced risk of cable entanglement and does not need sterilized cables.

Figure 19:
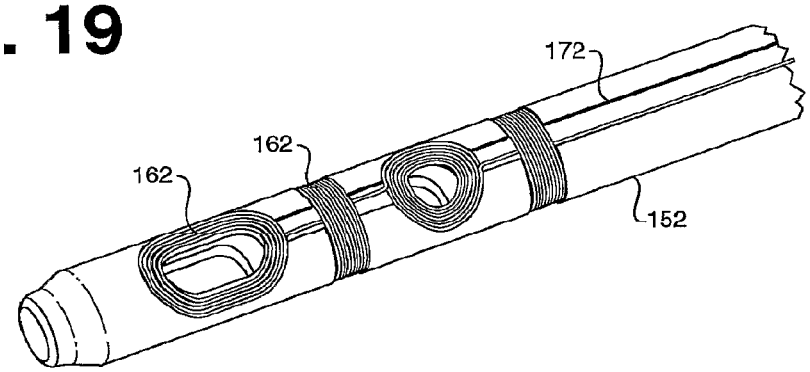
FIG. 19 is a front perspective view illustrating a first set and a second set of orthogonal driver coils.
Figure 20:
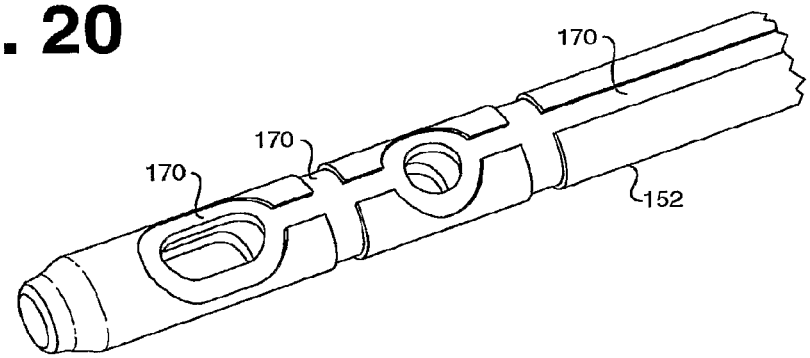
FIG. 20 is a front perspective of an intramedullary nail.

FIGS. 19 and 20 illustrate the instrumented medical implant 152. In the depicted embodiment, the implant 152 is an intramedullary nail. The instrumented medical implant 152 includes one or more recesses 170. The manufacturing route chosen for instrumenting the instrumented medical implant 152 is required to minimize any damage to the mechanical and physical properties of the implant and must be suitable for large scale commercialization. This can be confirmed by measuring the bending stiffness and fatigue behavior of the implant before and after instrumentation.

Incorporating sensors within the structure of internal implants raises the "packaging problem" of maintaining the insulation of the electronics, as biological tissues are an extremely hostile environment. Furthermore, the risk of damage to the printed circuit board (PCB) circuitry from common sterilization methods cannot be underestimated. In the embodiment depicted in FIGS. 19 and 20, the instrumented medical implant 152 is manufactured with the recess 170 to protect the coils 162 and associated conductor wires from abrasive damage during the surgical insertion process. The recess 170 may range in depth from about 0.1 millimeters to about 9 millimeters and is 0.5 millimeters in FIG. 20. The recesses 170 may be machined cavities.

In the embodiment depicted in FIG. 19, coils 162 are located in orthogonal pairs producing magnetic fields in response to an alternating current. These coils 162 are attached to the control circuit via conductor tracks 172 which are generally located longitudinally along the shank of instrumented medical implant 152. The coils 162 may be fixed to the surface of the recesses 170 using a range of high stiffness adhesives including epoxy resins, polyurethanes, ultraviolet light curable adhesives, and medical grade cyanoacrylates. These fixation methods do not adversely affect the performance of the coils 162.

The coils 170 are covered with a biocompatible potting material e.g., polyurethane or a silicone providing a hermetic seal. Polyurethane is of particular interest given its history of use for medical applications. Because the electronic components are sealed hermetically from the patient tissues and fluids, long term function of the device is achievable. At the same time, leakage of non-biocompatible or toxic materials is eliminated. The potting material is an electrically insulative, moisture resistant material, supplied in either a liquid or putty-like form and is used as a protective coating on sensitive areas of electrical and electronic equipment. It is available in two formats, one being optically opaque and the other colorless. The driver coils and conductors are covered in a potting material with suitable mechanical characteristics required to survive the implantation process and restore the mechanical envelope.

The coils 162 generate magnetic fields independently within a patient's body in response to a an alternating (AC) current driven at a frequency close to the upper frequency limit of audible sound (20 KHz). An oscillating circuit is an electric circuit with values of capacitance and inductance that cause its current, charge, and electric potential to oscillate in a sinusoidal pattern. The coil pairs 162 are embedded in the instrumented medical implant 152 such that their magnetic axes are orthogonal to each other and are at a fixed offset from the axis of the landmark. For each pair of oscillating circuits, the AC current frequency may be coupled independently to one of the drive coils resulting in one magnetic field being generated at any given time, referred to hereafter as time multiplexing. This provides independent sources of positional data. Multiplexing is defined as the transmission of multiple signals over a single communications line. Alternatively, the driver coils 162 may be frequency multiplexed enabling them to be driven simultaneously by a different alternating current frequency. This method is more simplified than time multiplexing given that is does not require the alternating application of AC currents to both driver coils. The positional data enables the precise location of both landmarks 160 to be determined independently by a landmark identifier which is positioned over a subject's bone. The instrumented medical implant 152 is designed such that each pair of coils 162 may be operated independently enabling landmarks 160 to be individually located by the user.

Figure 21:
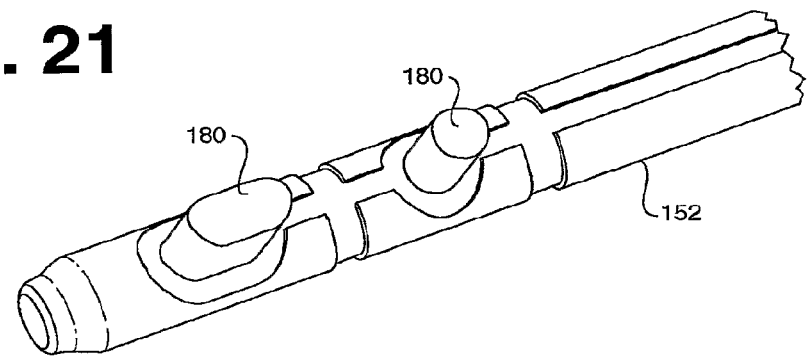
FIG. 21 is a front perspective view illustrating winding formers.

FIG. 21 illustrates one method for manufacturing the coils 162. In the embodiment depicted in FIG. 21, the instrumented medical implant 152 is an intramedullary nail. Once the machined cavities or recesses 170 have been produced both circumferentially and longitudinally in the instrumented medical implant 152, winding formers 180 are attached to the landmarks 160. An automatic coil winding machine to wind wire around the winding formers may be used to maximize the number of turns of copper in the circumferential plane. Winding coil wire onto the instrumented medical implant 152 in the longitudinal direction is more difficult to do given the lack of mechanical stability in that plane for winding purposes. The winding formers 180 enable the application of the necessary pressure during automatic winding in that particular plane in order to form the coils. Once all coils are in place, the coils are potted in epoxy.

Figure 22:
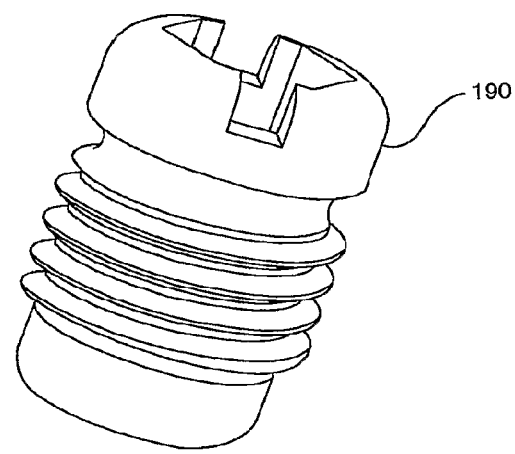
FIG. 22 is a front perspective view of a dummy nail cap insert.
Figure 23:
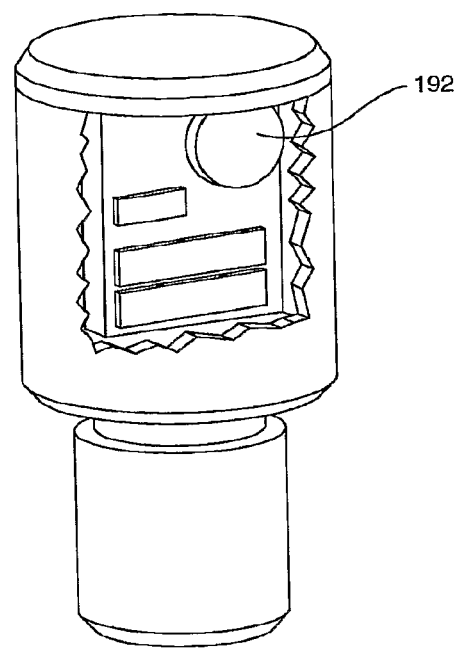
FIG. 23 is a front perspective view of an instrumented active insert.

FIG. 22 illustrates a dummy nail cap 190, and FIG. 23 illustrates an active nail cap 192. The active nail cap also may be termed an active nail head insert or a nail head. The dummy nail cap 190, which is usually provided with an intramedullary nail, can be replaced by the active nail cap 192. The active nail cap 192 provides the intramedullary nail with power and wireless communication. The telemetric intramedullary nail may include one or more of the following sub-systems: (a) a power supply, i.e. battery or energy scavenging device, or RF/Inductive power coupling systems, (b) measurement coupling systems, either RF or inductive, to create a complete instrumentation circuit with the passive components in the nail. An alternative to inductive/RF coupling is the use of slip rings or other physical connectors, (c) instrumentation amplifiers, signal processing and data storage systems, and (d) RF or inductively coupled communications devices for transmission of measurement data to off-implant, wearable or desk mounted data acquisition systems.

In this configuration, the intramedullary nail is implanted in the usual manner. Once the intramedullary nail has been implanted into bone, the dummy nail cap 190 is removed and the active nail head insert 192 is screwed into the threaded hole or otherwise seated in the proximal end portion of the intramedullary nail. This particular design avoids any sensitive electronics being damaged by the implantation process. Connections between the components in the nail head 192 and the instrumentation circuit in the nail shaft may be made using either an inductively coupled link or physical connections via slip rings. As an example, the active nail head 192 insert may include the control circuit and/or the power supply.

Figure 24:
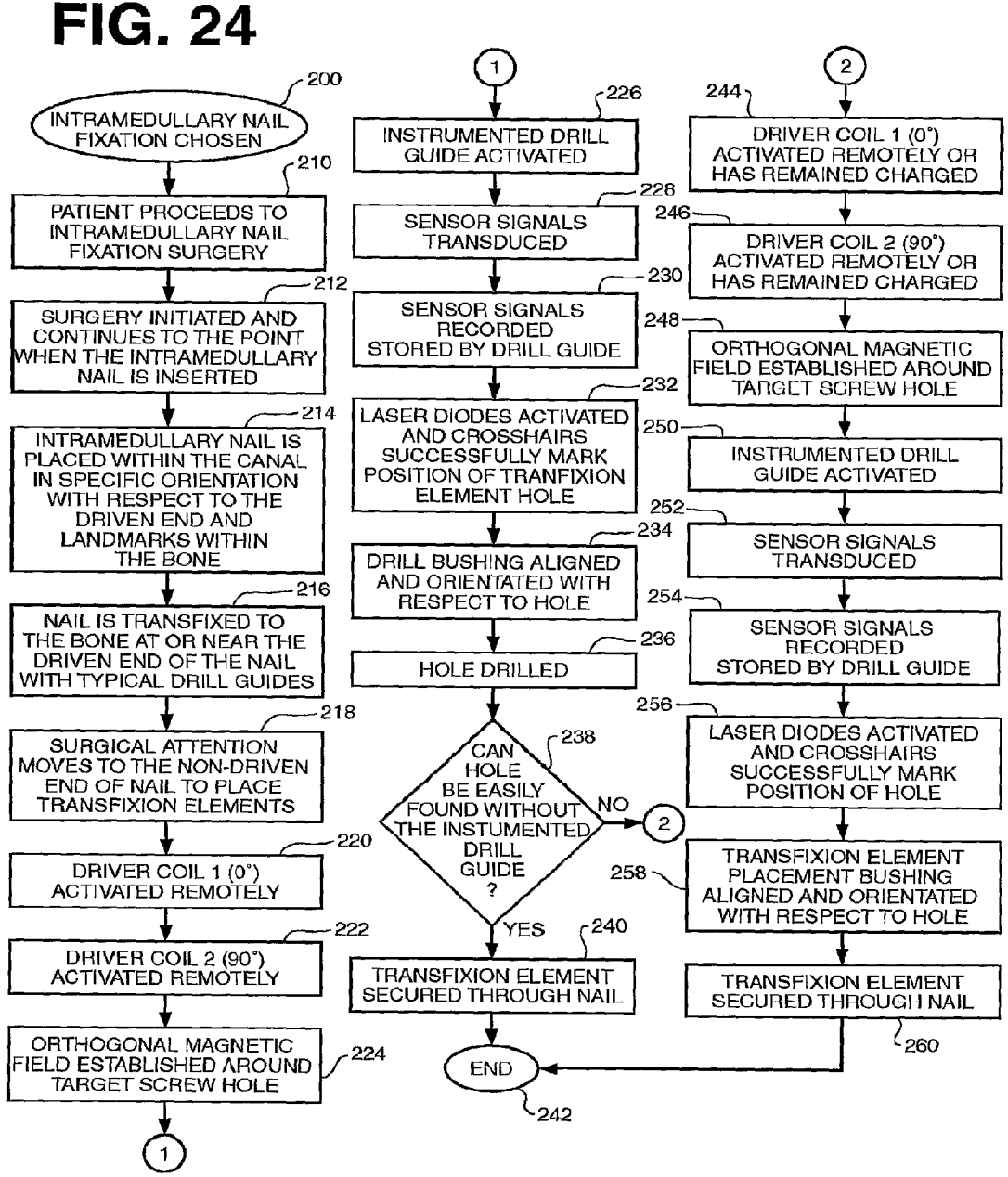
FIG. 24 is a flowchart that illustrates the process for targeting a distal screw.

A flow chart highlighting the process for targeting a landmark, such as targeting a distal screw hole, is shown in FIG. 24. The procedure is not affected by the instrumented devices in terms of the order in which the landmarks are located. However, the method of targeting is different in comparison to the conventional technique because it relies on the use of on-board coils and sensors to provide the user with a feedback signal. For example, continuous visual and/or sound information may be provided via a display screen of a computer. In the case of an intramedullary nail, this information enables the user to carry out the procedure in the usual manner by holding the drill guide and assembly in the correct position whilst making a stab incision in the tissue in the vicinity of the distal screw holes, drilling through the near and far cortices of the bone, and inserting and fastening the distal locking screws.

The process for targeting a landmark is generally the same regardless of the type of implant. In FIG. 24, the process is illustrated relative to an intramedullary nail, but those of ordinary skill in the art would understand that other types of implants may be used. Referring now to FIG. 24, intramedullary nail fixation is chosen in step 200. The patient proceeds to intramedullary nail fixation surgery in step 210. The surgery is initiated and continues until the intramedullary nail has been inserted in step 212. The intramedullary nail is placed within the canal in a specific orientation with respect to the driven end and landmarks within the bone in step 214. The nail is transfixed to the bone at or near the driven end of the nail with typical drill guides in step 216. This is significant in the case of an intramedullary nail because the driven end of the nail typically determines the orientation and position of the intramedullary nail. As such, transfixing this end first promotes achievement of the correct orientation of the nail and generally reduces the risk of later jeopardizing fracture reduction.

The surgical attention moves to the non-driven end of the nail to place transfixion elements in step 218. A first coil is activated remotely in step 220, and a second coil is activated remotely in step 222. In step 224, the orthogonal magnetic field established around the opening targets the locking screw. The instrumented drill guide is activated in step 226. The sensor signals are transduced in step 228. In an optional step, the sensor signals are recorded and stored by the drill guide in step 230. In an optional step, the laser diodes are activated and crosshairs mark the position of the transfixion element hole in step 232. In step 234, the drill guide is aligned and oriented with respect to the transfixion element hole. The hole is drilled in step 236. In step 238, a decision is made whether the hole can easily be found without the instrumented drill guide. If so, the transfixion element is secured through the nail in step 240. Steps 220 through 240 are repeated for each nail transfixion opening. In step 240, the process ends.

If the hole cannot be easily found, however, then the first coil is activated remotely or is maintained in a charged state in step 244. In step 246, the second driver coil is activated remotely or is maintained in a charged state. An orthogonal magnetic field is established around each target screw hole in step 248. The instrumented drill guide is activated in step 250. The sensor signals are transduced in step 252. In an optional step, the sensor signals are recorded and stored by the drill guide in step 254. In an optional step, the laser diodes are activated and the crosshairs mark the position of the transfixion hole in step 256. The transfixion element is aligned and oriented with respect to the transfixion hole in step 258. The transfixion elements are secured through the nail in step 260, and the process ends in step 242.

The invention also includes a method of targeting a landmark relative to an instrumented orthopaedic implant. The method includes the steps of: (a) installing an instrumented orthopaedic implant relative to a bone, the instrumented orthopaedic implant having at least one landmark and at least one corresponding coil proximate to the at least one landmark; (b) energizing the at least one corresponding coil; (c) orienting a landmark identifier relative to the energized at least one corresponding coil; (d) sensing the energized at least one corresponding coil; (e) processing the sensed at least one corresponding coil data to detect proximity of the landmark identifier relative to the energized at least one corresponding coil; and (f) providing a user with feedback information on the proximity of the landmark identifier relative to the energized at least one corresponding coil.

In some embodiments, the method further includes the step of placing a member through the bone and the instrumented orthopaedic implant. The member may be any number of devices. As examples, the member may be a drill, a tap, a screw, a peg, a pin, a staple, a wire, a provisional fixation device, a bar, a brad, a dowel, a fastener, a pipe, a rivet, a rod, a skewer, a sliding bar, a spike, a stake, a staple, or a stud.

In one embodiment, the method further includes the step of manually securing a portion of the instrumented orthopaedic implant. For example, this may include manually securing a proximal end of a femoral antegrade intramedullary nail or the distal end of a retrograde intramedullary nail.

In another embodiment, the method further includes the step of securing a portion of the implant using an instrument to aid in landmark identification. For example, this may include attaching a drill guide to an intramedullary nail and targeting an opening of the nail.

In yet another embodiment, the method further includes the step of energizing at least one other corresponding coil.

In some embodiments, the step of energizing the at least one corresponding coil includes the step of passively energizing the at least one corresponding coil. This may include coupling the at least one corresponding coil with an inductive power source.

In some embodiments, the step of energizing the at least one corresponding coil comprises the step of actively energizing the at least one corresponding coil.

In one embodiment, the method further includes the step of recording sensed data.

In another embodiment, the method further includes the step of emitting a magnetic field from the at least one corresponding coil.

In another embodiment, the step of sensing the energized at least one corresponding coil includes the step of monitoring field intensity of the energized at least one corresponding coil.

In still another embodiment, the method includes the steps of re-orienting the landmark identifier from a first position to a second position and comparing field intensity of the energized at least one corresponding coil between the first position and the second position.

In yet another embodiment, the landmark identifier identifies the largest field intensity.

In still another embodiment, the landmark identifier determines whether the field intensity at least meets a predetermined field intensity threshold.

In one particular embodiment, the feedback information provided is selected from the group consisting of audible, visual, and tactile. The audible feedback may be output through a speaker, headphones, ear buds, or an ear piece. The audible feedback signal may be transmitted over wire or wirelessly using radio frequency or terrestrial data transmission. The visual feedback may be output through a cathode ray tube, a liquid crystal display, or a plasma display. Visual feedback devices may include, as examples, a television monitor, a personal digital assistant, or a personal media player. The visual feedback signal may be transmitted over wire or wirelessly using radio frequency or terrestrial data transmission. The tactile feedback may be output through gloves, instruments, or a floor mat. The tactile feedback signal may be transmitted over wire or wirelessly using radio frequency or terrestrial data transmission.

In yet another embodiment, the method includes the steps of drilling an opening and installing a fastener through the drilled opening.

The technical solution described herein provides real-time, objective and accurate data for the distal targeting of locking screws in intramedullary nails for long bone fractures e.g. femur, tibia, fibula, hind foot and humerus. While distal targeting has been the focus, it is clear that targeting proximal holes in the nail is possible using this same technology. The instrumentation described herein can be applied to other trauma devices which require accurate placement in the target bone such as plates and external fixation devices. The instrumentation could also be extended to joint replacement implants such as total knee replacements (TKR) and total hip replacements (THR) in order to improve the outcome of a minimally invasive procedure which requires precise location of anatomical structures. The technology can also be extended to dental and craniomaxillofacial implants.

Alternate methods of charging the coil includes using a hand piece or drill sleeve that could inductively charge the coil and at the same time read the electromagnetic field. Similarly, the coil around the hole could be excited by a magnetic field created by a coil in the handheld reader for a very short period of time and then the handheld coil is switched off. Once excited, electrons would flow through the coil around the hole which then produces a magnetic field. At that point the handheld coil becomes a sensor, sensing the magnetic field created by the coils around the hole and the process is repeated until the handheld unit as it is moved around indicates the position and direction of the field/hole.

Alternate user interfaces include those to the Computer Assisted Surgery (CAS), robotic, or surgeon-free systems which usually includes a monitor showing moving illustrations of the implants and instruments in a simulated surgical field. This allows the user to place the screws in a video game-like environment. The interface could also be audible such as beeping similar to that of a metal detector used to find coins and other metal objects usually in fields. In this case as you would get closer to lining the drill up with the hole a beep would sound intermittently with a cadence that increases and once the drill is lined up a solid beep sound would be produced. Another means would be voice guidance similar to that of common voice guided navigation systems found at almost any retail shop and common to much of the public. Either of the listed sound guided methods could be produced with common wired or wireless speakers including headsets similar to that of the Bluetooth or other radio frequency data transmission ear pieces. Examples of this technology would be wireless Bluetooth headsets that are commonly paired with cellular telephones to enable the user to use the phone hands-free.

Alternate methods of incorporating the coils and wires into the implant include injection molding or casting the implant around these electrical components. This alleviates the need for potting materials and the tedious placement of the wires and coils. Similarly, the implant could be made from a long fiber composite, which typically is made in layers allowing for the coils and wires to be laid between layers within the composite material. Further, techniques exist today to print with metallic ink currently used in the RFID industry to print antennas on RFID tags. It is foreseen that with this technology the wires and coils could be printed on the implant after electrically isolating the to-be-printed surface of the implant. It would likely be necessary to electrically isolate the coils and wires after printing them. The ability to print the wires and coils allows for a tremendous increase in efficiency over any of the other methods as the process could is automatable, more precise, less costly, and more repeatable.

This technology enables transfixion holes in implants to be targeted without x-ray imaging. Further, if the implant has appropriate characteristics, the entire procedure could be done without any imaging assistance whatsoever. For example, an intramedullary nail containing two transfixion holes spans a fracture while maintaining one hole on either side of the fracture. In some cases the bone is curved and in turn forces the nails to deform elastically to accommodate the anatomy. This is especially evident when using intramedullary nails to treat femoral fractures. The technology herein allows for the nail to deform while still maintaining its ability to provide position and direction allowing for the surgeon to place the screws confidently within the bone transfixing the nail within.

This technology is suitable for applications outside of the orthopaedic industry such as any instance where precise positioning hole placement is necessary, manufacturing specifically product assembly, and finding items enshrouded thus not visible. In the instance of hole placement the coils could be printed on the item to be drilled and a machine (robotic arm) would detect the precise center of the hole using the technology herein and then drill or otherwise place the hole within the item. Similarly within manufacturing strategically placed coils could serve as datums alleviating the need for machine made or cast-in datums used as a basis for calculating or measuring other features on the item being manufactured. The datums would be referenced by a Computer Numerically Controlled (CNC) machine such as a lathe, mill, or machining center. Enshrouded items such as wall studs in a house, drainage pipes within concrete or walls, or hardware type screws buried within a wall for example. The coils could be placed on any of the items and excited as described herein and read with the reader described to locate these otherwise hard to find items.

The instrumented nail and drill guide described herein enables distal targeting to be carried out by surgeons who have not proficiently trained in the use of the C-arm technique. Furthermore, it eliminates the need for X-ray fluoroscopes, which are costly equipment in the operating rooms, most notably in the developing world where C-arms may not be available. Accurate drilling for distal screw placement also reduces operation time, debris from drilling onto the nail, x-ray exposure to both the patient and the surgeon, stress concentration around the drill hole due to correction drilling. Moreover, the technical solution increases surgeon comfort with the product. Further, this technology and device could be applied to proximal locking as well thus relieving the need for costly radiolucent proximal targeting devices. In some cases the holes proximally are not orthogonal to the long axis of the nail unlike most of the distal nail holes.

The technology and device could lead to easing the surgical procedure in remote surgical cases where the surgeon would not need to be in the operating room in which the patient is undergoing the surgery. Similarly incorporating this technology into an implant could allow for the surgery to be more easily automated and be performed robotically. Robotic surgery would increase the overall efficiency of the procedure as well as the accuracy in reduction, alignment, and screw placement. A compromise leading to robotic surgery might be the incorporation of this technology and device into the more common CAS system. This affords the CAS user an advantage over conventional CAS as the current CAS systems cannot account for the long term elastic implant deformation that is relatively common. The CAS systems only know the dimensions of the implant in its free state whereas the device herein accommodates the elastic deformation.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A system for targeting a landmark, the system comprising:
    a. an instrumented medical implant having a first landmark and a second landmark, the instrumented medical implant comprising:
        two or more first coils corresponding to the first landmark, wherein the first landmark is a first hole in the orthopaedic implant and the first coils are arranged to produce magnetic fields that designate a location and orientation of the first landmark; and
        two or more second coils corresponding to the second landmark, wherein the second landmark is a second hole in the orthopaedic implant and the second coils are arranged to produce magnetic fields that designate a location and orientation of the second landmark, the first coils being distinct from the second coils, the location of the first landmark being different from the location of the second landmark;
    b. a control circuit electrically connected to the first coils and the second coils, the control circuit being configured to selectively activate the first coils and the second coils to produce the magnetic fields that respectively designate the location of the first landmark or second landmark;
    c. a power supply electrically connected to the control circuit; and
    d. a landmark identifier having one or more magnetic sensors for sensing the magnetic fields produced by the first coils and the second coils.

2. The system of claim 1, wherein at least one of the first coils or second coils is disposed about an external surface of a shaft of the instrumented medical implant.

3. The system of claim 2, wherein the at least one of the first coils or second coils disposed about the external surface of the shaft of the instrumented medical implant is covered with a biocompatible material.

4. The system according to claim 1, wherein the instrumented medical implant is at least one of a bone plate, a bone screw, a bone peg, a bone staple, an intramedullary nail, an intramedullary nail cap, an intramedullary nail and plate combination, an interference screw, a hip replacement stem, a hip replacement femoral neck, a hip replacement femoral head, a hip replacement acetabular liner, a hip replacement acetabular shell, a knee replacement tibial tray, a knee replacement tibial tray liner, a knee replacement femoral component, a knee replacement tibial tray shaft extension, a knee replacement patellar implant, a knee replacement wedge, a trochlear groove implant, a femoral canal restrictor, a shoulder replacement humeral stem, a shoulder replacement glenoid component, a shoulder replacement humeral head, an elbow replacement humeral component, an elbow replacement radial component, an elbow replacement ulnar component, an ankle replacement tibial component, and an ankle replacement talar component.

5. The system according to claim 1, wherein the control circuit comprises an oscillator.

6. The system according to claim 1, wherein the control circuit comprises a multiplexer.

7. The system according to claim 1, wherein the power supply and control circuit are comprised of a single unit.

8. The system according to claim 1, wherein the power supply includes at least one of a capacitor, an inductive coupling, a battery, a mechanically driven power generation unit, a piezoelectric device, and an energy scavenging device.

9. The system according to claim 1, wherein the landmark identifier is selected from the group consisting of a drill guide, a drill sleeve, a drill, a drill nose, a drill barrel, a drill chuck, and a fixation element.

10. The system according to claim 1, wherein each of the one or more magnetic sensors is selected from the group consisting of a Hall effect sensor, a fluxgate magnetic field sensor, an inductive coil sensor, and a magneto-resistive sensor.

11. The system according to claim 1, wherein the power supply comprises an electromagnetic field generating coil.

12. The system according to claim 1, wherein at least one of the first coils is oriented generally orthogonal to one of the other first coils.

13. The system according to claim 1, wherein at least one of the first coils is oriented relative to another of the first coils having a relationship selected from the group consisting of generally oblique, offset, coplanar, parallel, collinear, and transverse.

14. The system according to claim 1, wherein the one or more magnetic sensors are configured to produce data indicative of proximity of the landmark identifier to the first landmark based on magnetic fields produced by the first coils, and the one or more magnetic sensors are configured to produce data indicative of proximity of the landmark identifier to the second landmark based on magnetic fields produced by the second coils.

15. The system according to claim 1, wherein each of the first coils is configured to be selectively activated without activating other first coils, and each of the second coils is configured to be selectively activated without activating other second coils.

16. The system according to claim 1, wherein one of the first coils extends around a perimeter of the first landmark, and one of the second coils extends around a perimeter of the second landmark.

17. A method of locating landmarks of an instrumented orthopaedic implant, the method comprising:
    installing an instrumented orthopaedic implant relative to a bone, the instrumented orthopaedic implant having two or more first coils corresponding to the first landmark and two or more second coils corresponding to the second landmark, the first coils being distinct from the second coils;
    activating the first coils to produce magnetic fields that indicate a location and orientation of the first landmark;
    obtaining first sensor data based on sensing the first coils;
    locating the first landmark based on the first sensor data independent of activation of the second coils;
    activating the second coils to produce magnetic fields that indicate a location and orientation of the second landmark;

obtaining second sensor data based on sensing the second coils; and locating the second landmark based on the second sensor data independent of activation of the first coils.

18. The method of claim 17, further comprising:

aligning a drill guide at the located first landmark;

drilling an opening through the bone and the instrumented orthopaedic implant while the drill guide is aligned at the located first landmark; and installing a fastener through the drilled opening.

19. The method of claim 18, further comprising:

aligning the drill guide at the located second landmark;

drilling a second opening through the bone and the instrumented orthopaedic implant while the drill guide is aligned at the located second landmark; and installing a second fastener through the second drilled opening.

20. The method of claim 17, further comprising activating at least one visual indicator.

21. The method of claim 20, wherein the at least one visual indicator is a light emitting diode.

22. The method according to claim 17, wherein at least one of the first landmark and the second landmark is an opening.

23. The method of claim 17, wherein the instrumented orthopaedic implant is an intramedullary nail.

24. The method of claim 17, further comprising recording the first sensor data and the second sensor data.

25. A system for targeting a landmark, the system comprising:

a. an instrumented medical implant having a shaft and at least one landmark, the at least one landmark having a first corresponding coil that extends around an exterior portion of the shaft of the instrumented medical implant and a second corresponding coil that extends around a perimeter of the at least one landmark;

b. a control circuit electrically connected to the first coil and the second coil;

c. a power supply electrically connected to the control circuit; and d. a landmark identifier having a magnetic sensor for sensing the first coil and the second coil.

26. The system of claim 25, wherein the at least one landmark of the medical implant is a hole defined through the shaft of the instrumented medical implant, and the second corresponding coil extends around a perimeter of the hole.

27. A system for targeting a landmark, the system comprising:

a. an instrumented medical implant having a first landmark and a second landmark, the instrumented medical implant comprising two or more first coils corresponding to the first landmark and two or more second coils corresponding to the second landmark, the first coils being distinct from the second coils, wherein the instrumented medical implant defines a longitudinal groove in an exterior of the instrumented medical implant, and wherein the instrumented medical implant comprises one or more conductor wires for connecting the first coils and the second coils to a current source, the one or more conductor wires being disposed in the longitudinal groove;

b. a control circuit electrically connected to the first coils and the second coils, the control circuit being configured to selectively activate the first coils and the second coils;

c. a power supply electrically connected to the control circuit; and d. a landmark identifier having one or more magnetic sensors for sensing the first coils and the second coils.

* * * * *